US008278413B2

(12) United States Patent
Bonny

(10) Patent No.: US 8,278,413 B2
(45) Date of Patent: *Oct. 2, 2012

(54) CELL-PERMEABLE PEPTIDE INHIBITORS OF THE JNK SIGNAL TRANSDUCTION PATHWAY

(75) Inventor: Christophe Bonny, Lausanne (CH)

(73) Assignee: Xigen SA, Laussanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/222,115

(22) Filed: Aug. 31, 2011

(65) Prior Publication Data
US 2012/0142613 A1 Jun. 7, 2012

Related U.S. Application Data

(62) Division of application No. 10/110,430, filed as application No. PCT/IB00/01538 on Oct. 12, 2000, now Pat. No. 8,183,339, which is a division of application No. 09/503,954, filed on Feb. 14, 2000, now Pat. No. 6,610,820.

(60) Provisional application No. 60/158,774, filed on Oct. 12, 1999.

(51) Int. Cl.
*C12N 9/00* (2006.01)
*A61K 38/00* (2006.01)

(52) U.S. Cl. .......................... 530/300; 514/1.1
(58) Field of Classification Search .................. None
See application file for complete search history.

(56) References Cited

U.S. PATENT DOCUMENTS

| | | | |
|---|---|---|---|
| 4,631,211 A | 12/1986 | Houghten | |
| 4,698,327 A | 10/1987 | Nagarajan et al. | |
| 4,732,890 A | 3/1988 | Bonelli et al. | |
| 5,169,933 A | 12/1992 | Anderson et al. | |
| 5,597,895 A | 1/1997 | Gaynor et al. | |
| 5,670,617 A | 9/1997 | Frankel et al. | |
| 5,672,479 A | 9/1997 | Johnson et al. | |
| 5,674,980 A | 10/1997 | Frankel et al. | |
| 5,686,264 A | 11/1997 | Gaynor et al. | |
| 5,747,641 A | 5/1998 | Frankel et al. | |
| 5,756,684 A | 5/1998 | Johnson et al. | |
| 5,804,604 A | 9/1998 | Frankel et al. | |
| 5,840,313 A | 11/1998 | Vahlne et al. | |
| 5,989,814 A | 11/1999 | Frankel et al. | |
| 5,994,108 A | 11/1999 | Gaynor et al. | |
| 5,994,109 A | 11/1999 | Woo et al. | |
| 6,043,083 A | 3/2000 | Davis et al. | |
| 6,117,632 A | 9/2000 | O'Mahony | |
| 6,284,456 B1 | 9/2001 | Jones et al. | |
| 6,300,317 B1 | 10/2001 | Szoka, Jr. et al. | |
| 6,316,003 B1 | 11/2001 | Frankel et al. | |
| 6,348,185 B1 | 2/2002 | Piwnica-Worms | |
| 6,448,283 B1 | 9/2002 | Ylikoski et al. | |
| 6,495,663 B1 | 12/2002 | Rothbard et al. | |
| 6,586,403 B1 | 7/2003 | Mathison et al. | |
| 6,610,820 B1 | 8/2003 | Bonny | |
| 6,630,351 B1 | 10/2003 | Monahan et al. | |
| 6,653,443 B2 | 11/2003 | Zhang et al. | |
| 6,740,524 B1 | 5/2004 | Akuta et al. | |
| 6,780,970 B2 | 8/2004 | Bonny | |
| 6,881,825 B1 | 4/2005 | Robbins et al. | |
| 6,960,648 B2 | 11/2005 | Bonny | |
| 7,034,109 B2 | 4/2006 | Bonny | |
| 2002/0103229 A1 | 8/2002 | Bhagwat et al. | |
| 2003/0100549 A1 | 5/2003 | Salituro et al. | |
| 2003/0104622 A1 | 6/2003 | Robbins et al. | |
| 2003/0108539 A1 | 6/2003 | Bonny | |
| 2003/0124113 A1 | 7/2003 | Hillman et al. | |
| 2003/0220480 A1 | 11/2003 | Bonny | |
| 2004/0082509 A1 | 4/2004 | Bonny | |
| 2004/0265879 A1 | 12/2004 | Iversen et al. | |
| 2005/0059597 A1 | 3/2005 | Tymianski | |
| 2005/0106695 A1 | 5/2005 | Bonny | |
| 2006/0258706 A1 | 11/2006 | Saindane et al. | |
| 2006/0270646 A1 | 11/2006 | Graczyk et al. | |
| 2007/0003531 A1 | 1/2007 | Mukherji et al. | |
| 2008/0008749 A1 | 1/2008 | Pearlman et al. | |

FOREIGN PATENT DOCUMENTS

| | | |
|---|---|---|
| EP | 0679716 A1 | 11/1995 |
| EP | 0 897 002 A2 | 2/1999 |
| EP | 1364949 A1 | 11/2003 |
| FR | 2767323 A1 | 2/1999 |
| JP | 58-146538 | 9/1983 |
| JP | 02-221294 | 4/1990 |
| JP | 04-66595 | 10/1992 |
| JP | 7-503617 | 4/1994 |
| JP | 2002-534479 A | 10/2002 |
| WO | 92-18138 A1 | 10/1992 |
| WO | 93/18759 | 9/1993 |
| WO | 94-04686 A1 | 1/1994 |
| WO | 94/04562 | 3/1994 |
| WO | 94/05311 | 3/1994 |
| WO | 94/23751 | 10/1994 |
| WO | 95-34295 A1 | 12/1995 |
| WO | 97-05265 A1 | 2/1997 |
| WO | 97-10836 A1 | 3/1997 |
| WO | 98-11907 A1 | 3/1998 |

(Continued)

OTHER PUBLICATIONS

133:204452, 2000, Chemical Abstracs Database, XP002554007.
AAD22543, 2007, GenBank, 2 pages.
Aarts et al., 2002, Science, pp. 846-850.
AF074091, 2007, GenBank, 2 pages.
Aldrian-Herrada et al, 1998, Nucleic Acids Research, pp. 4910-4916.
Assi Kiran et al, 2006, Immunology, pp. 112-121.
Ausubel, 1988, Current Protocols in Molecular Biology, pp. 6.4.01-6.4.10.
Berendsen et al., 1998, Science, pp. 642-643.
Besalle et al., 1990, Febs Letters, pp. 151-155.
Bonny et al., 1995, Molecular Endrocrinology, pp. 1413-1426.
Bradford et al., 1994, Nature, pp. 744-746.
Bradley et al., 2002, J. Mol. Biol., pp. 373-386.
Branden et al., 1999, Nat. Biotechnol., pp. 784-787.
Lim Jun Man et al, 2003, Journal of Cosmetic Science, pp. 483-491.
Cardozo et al., 2007, Biochimica et Biophysica Acta, pp. 2222-2234.
Chaloin et al., 1998, Biochem. Biophys. Res. Commun., pp. 601-608.
Chemical Approaches to the Synthesis of Peptides and Proteins, pp. 209-236, 1997.

(Continued)

*Primary Examiner* — Suzanne M Noakes
*Assistant Examiner* — Jae W Lee
(74) *Attorney, Agent, or Firm* — Morgan, Lewis & Bockius LLP

(57) ABSTRACT

The invention provides cell-permeable peptides that bind to JNK proteins and inhibit JNK-mediated effects in JNK-expressed cells.

7 Claims, 9 Drawing Sheets

FOREIGN PATENT DOCUMENTS

| | | |
|---|---|---|
| WO | 98/23781 | 6/1998 |
| WO | 98-44106 A1 | 10/1998 |
| WO | 98-47913 A1 | 10/1998 |
| WO | 98-49188 A1 | 11/1998 |
| WO | 98/51325 | 11/1998 |
| WO | 98/51825 | 11/1998 |
| WO | 98-52614 A1 | 11/1998 |
| WO | 99/07728 | 2/1999 |
| WO | 99/16787 | 4/1999 |
| WO | 99-49879 A1 | 10/1999 |
| WO | 99/50282 | 10/1999 |
| WO | 99/58561 | 11/1999 |
| WO | 99/67284 | 12/1999 |
| WO | 00/12587 | 3/2000 |
| WO | 00-41719 A1 | 7/2000 |
| WO | 01/10888 A1 | 2/2001 |
| WO | 01/13957 A2 | 3/2001 |
| WO | 01/15511 A2 | 3/2001 |
| WO | 01-27268 A2 | 4/2001 |
| WO | 02/31109 A2 | 4/2002 |
| WO | 02/061105 A2 | 8/2002 |
| WO | 02/062396 A2 | 8/2002 |
| WO | 02/065986 A2 | 8/2002 |
| WO | 02/069930 A1 | 9/2002 |
| WO | 02-81504 A2 | 10/2002 |
| WO | 02/081505 A2 | 10/2002 |
| WO | 03/075917 A1 | 9/2003 |
| WO | 03/103698 A1 | 12/2003 |
| WO | 03/103718 A2 | 12/2003 |
| WO | 2004/022580 A2 | 3/2004 |
| WO | 2004/035793 A1 | 4/2004 |
| WO | 2004/045535 A2 | 6/2004 |
| WO | 2004/054501 A2 | 7/2004 |
| WO | 2004/070052 A2 | 8/2004 |
| WO | 2004/092339 A2 | 10/2004 |
| WO | 2005/084158 A2 | 9/2005 |
| WO | 2005/097116 A1 | 10/2005 |
| WO | 2007/031098 A1 | 3/2007 |
| WO | 2008/028860 A1 | 3/2008 |
| WO | 2009/143864 A1 | 12/2009 |
| WO | 2009/143865 A1 | 12/2009 |

OTHER PUBLICATIONS

Chemical Approaches to the Synthesis of Peptides and Proteins, pp. 237, 264-267, 1997.
Combinatorial Peptide and Nonpeptide Libraries, VCH, pp. 139-171, 1997.
Combinatorial Peptide and Nonpeptide Libraries, VCH, pp. 327-347, 1997.
Database WPI, 2010, Thomson Scientific, Table 1, 1-4_XP002643212.
Derossi et al., 1996, Journal of Biological Chemistry, pp. 18188-18193.
Designing Custom Peptides, 2004, Sigma Genosys, pp. 1-2.
Diabetes (2001), vol. 50, No. supplement 2, ppA294(1217-P).
Dietz et al, 2004, Molecular and Cellular Neurosciences, pp. 85-131.
Dominguez-Bendala et al., 2005, Diabetes, pp. 720-726.
Fornoni et al., 2007, Biochem Biophys Res Comm, pp. 227-233.
Frankel et al., 1988, Cell Press, pp. 1189-1193.
Futaki et al., 2001, Journal of Biological Chemistry, pp. 5836-5840.
Gammon et al, 2003, Bioconjugate Chemistry, pp. 368-376.
Guichard et al., 1994, PNAS, pp. 9765-9769.
Gunaseelan et al, Bioconjugate Chemistry, pp. 1322-1333, 2 0 0 4.
Hawiger, 1999, Curr. Opin. Chem. Biol., pp. 89-94.
Hayashi et al., 2007, Bioorganic & Medicinal Chemistry Letters, pp. 5129-5132.
Herve et al., 1997, Mol Immunol, pp. 157-163.
Hillier et al, 1995, EMBL Sequence Database, R85141.
Ho et al, 2001, Cancer research, pp. 474-477.
Holinger et al, 1999, Journal of Biological Chemistry, pp. 13298-13304.
Holzberg et al., 2003, Journal of Biological Chemistry, pp. 40213-40223.
Houghten, 1985, PNAS, pp. 5131-5135.
Johnson et al., 2007, Biochmica et Biophysica Acta, pp. 1341-1348.
Kida et al., 2006, Bioorganic & Medicinal Chemistry Letters, pp. 743-745.
Kieber-Emmons et al., 1997, Curr.Opin. Biotechnol., pp. 435-441.
Kisselev, 2002, Structure, pp. 8-9.
Lewis et al, 2003, Journal of Labelled Compounds and Radiopharmaceuticals, pp. S13.
Pennington, Michael W. and Dunn, Ben M. (Editors)—Chapter 11—Design of Novel Synthetic Peptides including Cyclic Conformationally and Topgraphically Constrained Analogs—Hruby, Victor and Bonner, G. Gregg—Methods in Molecular Biology—vol. 35—Peptide Synthesis Protocols—1994—pp. 201-239—Humana Press Inc.—USA.
Pirvola et al.—Rescue of Hearing, Auditory Hair Cells, and Neurons by CEP-1347/KT7515, an Inhibitor of c-Jun N-Terminal Kinase Activation—The Journal of Neuroscience pp. 43-50—vol. 20—No. 1—Society of Neuroscience—USA, Jan. 1, 2000.
Ramage, Robert and Epton, Roger (Editors)—Chapters 165 and 166—Guichard et al.—Chapter 167—Gur'Yanov et al.—EPS—Proceedings of the Twenty-Fourth European Peptide Symposium, Sep. 8-13, 1996, Edinburgh, Scotland—pp. 447-451—The European Peptide Society—Mayflower Scientific Ltd.—United Kingdom.
Ramage, Robert and Epton, Roger (Editors)—Chapter—183—Horvath et al.—Chapter 184—Hruby et al.—EPS—Proceedings of the Twenty-Fourth European Peptide Symposium, Sep. 8-13, 1996, Edinburgh, Scotland—pp. 483-486—The European Peptide Society—Mayflower Scientific Ltd.—United Kingdom.
Rickels et al.—Phage Display Selection of Ligand Residues Important for Src Homology 3 Domain Binding Specificity—Biochemistry—Proceedings of the National Academy of Science—Nov. 1995—pp. 10909-10913—vol. 92—National Academy of Science—USA.
Roduit, Raphaël and Schorderet, Daniel F.—MAP Kinase Pathways in UV-Induced Apoptosis of Retinal Pigment—Epithelium ARPE19 Cells—Apoptosis—2008—pp. 343-353—DOI 10.1007/s10495-008-0179-8—Springer Science+Business Media, LLC—USA.
Rojas et al.—Controlling Epidermal Growth Factor (EGF)—Stimulated Ras Activation in Intact Cells by a Cell-Permeable Peptide Mimicking Phosphorylated EGF Receptor—Journal of Biological Chemistry—Nov. 1, 1996—pp. 27456-27461—vol. 271—No. 44—The American Society for Biochemistry and Molecular Biology, Inc.—USA.
Ruben et al.—Structural and Functional Characterization of Human Immunodeficiency Virus tat Protein—Journal of Virology—Jan. 1989—pp. 1-8—vol. 63—No. 1—American Society for Microbiology—USA.
Rudikoff et al.—Single Amino Acid Substitution Altering Antigen-Binding Specificity—Immunology—Proceedings of the National Academy of Science—Mar. 1982—pp. 1979-1983—vol. 79—National Academy of Science—USA.
Rudinger, J.—Characteristics of the Amino Acids as Components of a Peptide Hormone Sequence—Peptide Hormones—1976—pp. 1-7—University Park Press, Baltimore—USA.
Schwarze et al.—in Vivo Protein Transduction: Delivery of a Biologically Active Protein into the Mouse—Science—Sep. 3, 1999—pp. 1569-1572—vol. 285—Science Magazine—USA.
Shimonishi, Yasutsuga (Editor)—Oehlke et al.—Rapid Translocation of Amphipathic α-Helical and β-Sheet-Forming Peptides through Plasma Membranes of Endothelian Cells—pp. 282-783—Van Regenmortel et al.—Peptide Analogues as Vaccines and Immunomodulators—pp. 784-787—Saito, N. G. and Paterson, Y.—Contributation of Peptide Backbone Atoms to Binding of an Antigenic Peptide to Class I Major Histocompatibility Complex Molecule—pp. 805-807—Peptide Science—Present and Future—Kluwer Academic Publishers—United, 1999.
Smilek et al.—A Single Amino Acid Change in a Myelin Basic Protein Peptide Confers the Capacity to Prevent Rather than Induce Experimental Autoimmune Encephalomyelitis—Immunology—Proceedings of the National Academy of Science—Nov. 1, 1991—pp. 9633-9637—vol. 88—No. 21—The National Academy of Science—USA.
Thoren et al.—The Antennapedia Peptide Penetratin Translocates across Lipid Bilayers—The First Direct Observation—FEBS Letters—2000—pp. 265-268—No. 482—Federation of European Biochemical Societies - Elsevier Science B.V. - Europe.

Torgerson et al.—Regulation of NF-kappa B, AP-1, NFAT, and STAT1 Nuclear Import in T Lymphocytes by Noninvasive Delivery of Peptide Carrying the Nuclear Localization Sequence of NF-kappa B p50—Journal of Immunology—1998—pp. 6084-6092—vol. 161—The American Association of Immunologists—USA.

Touchard et al.—A Peptide Inhibitor of c-Jun N-Terminal Kinase for the Treatment of Endotoxin-Induced Uveitis-Immunology and Microbiology—Investigative Ophthalmology & Visual Science—Sep. 2010—pp. 4683-4693—vol. 51—No. 9—Association for Research in Vision and Ophthalmology—USA.

Tournier et al.—Mitogen-Activated Protein Kinase Kinase 7 is an Activator of the c-Jun NH2-Terminal Kinase—Cell Biology—Proceedings of the National Academy of Science—Jul. 1997—pp. 7337-7342—vol. 94—National Academy of Science—USA.

Van Regenmortel et al.—D-Peptides as Immunogens and Diagnostic Reagents—Protein Engineering—Current Opinion of Biotechnology—1998—pp. 377-382—vol. 8—Current Biology Publications—France.

Vives et al.—A Truncated HIV-1 Tat Protein Basic Domain Rapidly Translocates Through the Plasma Membrane and Accumulates in the Cell Nucleus—Journal of Biological Chemistry—Jun. 20, 1997—pp. 16010-16017—vol. 272—No. 25—The American Society for Biochemistry and Molecular Biology, Inc.—USA.

Vives et al.—Structure-Activity Relationship Study of the Plasma Membrane Translocating Potential of a Short Peptide from HIV-1 Tat Protein—Letters in Peptide Science—1997—pp. 429-436—vol. 4—Kluwer Academic Publishers—The Netherlands.

Vocero-Akbani et al.—Killing HIV-Infected Cells by Transduction with an HIV Protease-Activated Caspase-3 Protein—Nature Medicine—Jan. 1999—pp. 29-33—vol. 5—No. 1—Nature America Inc.—USA.

Voet, Donald and Voet, Judith G.—Abnormal Hemoglobins—1995—pp. 235-241—Biochemistry Second Edition—John Wiley & Sons, Inc.—USA.

Waldmeier et al.—Recent Clinical Failures in Parkinson's Disease with Apoptosis Inhibitors Underline the Need for a Paradigm Shift in Drug Discovery for Neurodegenerative Diseases—Biochemical Pharmacology—Nov. 15, 2006—pp. 1197-1206—vol. 72—No. 10—ScienceDirect—Elsevier Inc.—USA.

Whitmarsh, A.J. and Davis, R.J.—Transcription Factor AP-1 Regulation by Mitogen-Activated Protein Kinase Signal Transduction Pathways—Review—Journal of Molecular Medicine Oct. 7, 1996—pp. 589-607—vol. 74—No. 10—Springer-Verlag—USA.

Wilson, David—Preventing Nerve Cell Death in ALS—Internet document—<http://www.als.caJ_news/57.aspx>—Dec. 5, 2001—2 pages—USA.

Yang et al.—Differential Targeting of MAP Kinases to the ETS-Domain Transcription Factor Elk-1—The EMBO Journal—1998—pp. 1740-1749—vol. 17—No. 6—European Molecular Biology Organisation—Oxford University Press—United Kingdom.

Yasuda et al.—The JIP Group of Mitogen-Activated Protein Kinase Scaffold Proteins—Molecular and Cellular Biology—Oct. 1999—pp. 7245-7254—vol. 19—No. 10—American Society for Microbiology—USA.

Zhang et al.—Preparation of Functionally Active Cell-Permeable Peptides by Single-Step Ligation of Two Peptide Modules—Proceedings of National Academy of Sciences—Biochemistry—Aug. 1998—pp. 9184-9189—vol. 95—National Academy of Sciences—USA.

NCBI Sequence Viewer—Accession No. AAD20443—Reports—Islet-Brain 1 (Homo Sapiens)—Two References—Mooser et al.—Mar. 17, 1999—2 pages—USA.

NCBI Sequence Viewer—Accession No. AAD22543—Reports—Islet-Brain 1 (Rattus Norvegicus)—Three References—Bonny et al.—Mar. 1, 2006—2 pages USA.

NCBI Sequence Viewer—Accession No. AAF32323—Reports—Islet-Brain 2 (Homo Sapiens)—Two References—Negri et al.—Feb. 9, 2000—2 pages—USA.

NCBI Sequence Viewer—Accession No. AF074091—Reports—Homo Sapiens Islet-Brain 1 mRNA—Complete Cds.—Two References—Mooser et al.—Mar. 17, 1999—2 pages—USA.

NCBI Sequence Viewer—Accession No. AF108959—Reports—Rattus Norvegicus Islet-Brain 1 (IB1) mRNA—Complete Cds.—Three References—Bonny et al.—Mar. 1, 2006—2 pages—USA.

NCBI Sequence Viewer—Accession No. AF218778—Reports—Homo Sapiens Islet-Brain 2 mRNA—Complete Cds—Three References—Kristensen et al.—Mar. 2, 2006—2 pages—USA.

NCBI Sequence Viewer—Accession No. PH0878—Reports—Ig Kappa Chain V Region (Anti-DNA, SNA)—Human (Fragment) One Reference—Manheimer-Lory et al.—May 30, 1997—1 page—USA.

Abaza et al.—Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin—Journal of Protein Chemistry—1992—pp. 433-444—vol. 11—No. 5—USA.

Adele-Biassette et al.—Neuronal Apoptosis does not Correlate with Dementia in HIV Infection but is Related to Microglial Activation and Axonal Damage—Neuropathology and Applied Neurobiology—1999—pp. 123-133—vol. 25—Blackwell Science Ltd.—USA.

Adler, et al.—Regulation of JNK Signaling by GSTp—The EMBO Journal—Mar. 1, 1999—pp. 1321-1334—vol. 18—No. 5—European Molecular Biology Organization—USA.

Ahmed, Shafiq Uddin and Milner, Jo—Basal Cancer Cell Survival Involves JNK2 Suppression of a Novel JNK1/c-Jun/Bcl-3 Apoptotic Network—PLoS ONE—Oct. 2009—pp. 1-13—vol. 4—Issue 10—University of York—United Kingdom.

Agrawal, Vishal and Kishan, K.V. Radha—Promiscuous Binding Nature of SH3 Domains to their Target Proteins—Protein and Peptide Letters—2002—pp. 185-193—vol. 9—No. 3—Bentham Science Publishers Ltd.—USA.

Barr et al.—Identification of the Critical Features of a Small Peptide Inhibitor of JNK Activity—Mar. 20, 2002—pp. 10987-10997—vol. 277—No. 13—USA.

Bonny et al., Cell-Permeable Peptide Inhibitors of JNK: Novel Blockers of Beta-Cell Death—Diabetes—Jan. 2001—pp. 77-82—vol. 50—No. 1—USA.

Bonny et al.—IB1, A JIP-1-Related Nuclear Protein Present in Insulin-Secreting Cells—Journal of Biological Chemistry—Jan. 23, 1998—pp. 1843-1846—vol. 273—No. 4—USA.

Bonny et al.—Targeting the JNK Pathway as a Therapeutic Protective Strategy for Nervous Systems Diseases—2005—pp. 57-67—vol. 16—No. 1—Freund & Pettman—United Kingdom.

Borsello et al.—A Peptide Inhibitor of c-Jun N-Terminal Kinase Protects Against Excitotoxicity and Cerebral Ischemia—Aug. 24, 2003 (Sep. 2003)—pp. 1180-1186 —vol. 9—No. 9—Nature Medicine—USA.

Borsello, Tiziana and Bonny, Christophe—Use of Cell-Permeable Peptides to Prevent Neuronal Degeneration—Trends in Molecular Medicine—May 2004—pp. 239-244—vol. 10—No. 5—Elsevier Ltd—www.sciencedirect.com—USA.

Brady, Leo and Dodson, Guy—Reflections on a Peptide—Nature—News and Views—Drug Design—Apr. 21, 1994—pp. 692-693—vol. 368 (6473)—Nature Publishing Group—USA.

Branden, Carl and Tooze, Carl—Introduction to Protein—Second Edition—1999—Garland Publishing, Inc.—p. 382—USA.

Branden, Carl and Tooze, Carl—Introduction to Protein—1991—Garland Publishing, Inc.—p. 247—USA.

Briand et al—A Retro-Inverso Peptide Corresponding to the GH Loop of Foot-and-Mouth Disease Virus Elicits High Levels of Long-Lasting Protective Neutralizing Antibodies—Proceedings of National Academy of Sciences—Immunology—Nov. 1997—pp. 12545-12550—vol. 94—National Academy of Sciences—USA.

Brugidou et al.—The Retro-Inverso Form of a Homeobox-Derived Short Peptide is Rapidly Internalized by Cultured Neurons: A New Basis for an Efficient Intracellular Delivery System—Biochemical and Biophysical Research Communications—Sep. 14, 1995—pp. 685-693—vol. 214—No. 2—Academic Press, Inc.—USA.

Chie et al.—Identification of the Site of Inhibition of Oncogenic ras-p21-Induced Signal Transduction by a Peptide from a Ras Effector Domain—Journal of Protein Chemistry—Nov. 4, 1999—pp. 881-884—vol. 18—No. 8—USA.

Chorev et al.—A Dozen Years of Retro-Inverso Peptidomimetics—Accounts of Chemical Research—1993—pp. 266-273—vol. 26—American Chemical Society—USA.

Chorev et al.—Recent Developments in Retro Peptides and Proteins—An Ongoing Topochemical Exploration—Oct. 1995—pp. 438-445—vol. 13—No. 10—TIBTECH (Trends in Biotechnology) Elsevier Science Ltd.—USA.

Creighton, Thomas E. (Editor )—Janin, Jaël—Protein—Protein Interactions—Encyclopedia of Molecular Biology—1999—pp. 2027-2033—vol. 1—A Wiley-Interscience Publication—John Wiley & Sons, Inc.—USA.

Dang et al.—Nuclear and Nucleolar Targeting Sequences of c-erb-A, c-myb, N-myc, p53, HSP70, and HIV tat Proteins—Journal of Biological Chemistry—Oct. 25, 1989—pp. 18019-18023—vol. 264—No. 30—The American Society for Biochemistry and Molecular Biology, Inc.—USA.

Dickens et al.—Database—UNIPROT—Retrieved from EBI—Database Accession No. Q9WVI9—Abstracts—Feb. 28, 2003—Document No. XP-002366175—USA.

Dickens et al.—A Cytoplasmic Inhibitor of the JNK Signal Transduction Pathway—Science—Aug. 1, 1997—pp. 693-696—vol. 277—No. 5326—Science Magazine—USA.

Elliott et al.—Intercellular Trafficking and Protein Delivery by a Herpesvirus Structural Protein—Cell—Jan. 24, 1997—pp. 223-233—vol. 88—No. 2—Cell Press—United Kingdom.

Fawell et al.—Tat-Mediated Delivery of Heterologous Proteins into Cells—Cell Biology—Proceedings of the National Academy of Sciences—Jan. 8, 1994—pp. 664-668—vol. 91—Biogen Inc.—USA.

Fischer, P.M.—The Design, Synthesis and Application of Stereochemical and Directional Peptide Isomers: A Critical Review—Current Protein and Peptide Science—2003—pp. 339-356—vol. 4—Bentham Science Publishes Ltd.—United Kingdom.

Frankel et al.—Activity of Synthetic Peptides from the Tat Protein of Human Immunodeficiency Virus Type 1—Proceedings of National Academy of Sciences—Biochemistry—Oct. 1989—pp. 7397-7401—vol. 86—National Academy of Sciences—USA.

Giorello et al—Inhibition of Cancer Cell Growth and c-Myc Transcriptional Activity by a c-Myc Helix 1-Type Peptide Fused to an Internalization Sequence—Cancer Research—Aug. 15, 1998—pp. 3654-3659—vol. 58—USA.

Gotthardt et al.—Interactions of the Low Density Lipoprotein Receptor Gene Family with Cytosolic Adaptor and Scaffold Proteins Suggest Diverse Biological Functions in Cellular Communication and Signal Transduction—The Journal of Biological Chemistry—Aug. 18, 2000—pp. 25616-25624—vol. 275—No. 33—The American Society for Biochemistry and Molecular Biology, Inc.—USA.

Guichard et al.—Partially Modified Retro-Inverso Pseudopeptides as Non-Natural Ligands for the Human Class I Histocompatibility Molecule HLA-A2—Journal of Medicinal Chemistry—1996—pp. 2030-2039—vol. 39—American Chemical Society—USA.

Gura, Trisha—Cancer Models: Systems for Identifying New Drugs Are Often Faulty—Science—Nov. 7, 1997—pp. 1041-1042—No. 278 (5340)—USA.

Hauber et al.—Mutational Analysis of the Conserved Basic Domain of Human Immunodeficiency Virus tat Protein—Journal of Virology—Mar. 1989—pp. 1181-1187—vol. 63—No. 3—American Society of Microbiology—USA.

Heemskerk et al.—From Chemical to Drug: Neurodegeneration Drug Screening and the Ethics of Clinical Trials—Commentary—Nature Neuroscience Supplement—Nov. 2002—pp. 1027-1029—vol. 5—Nature Publishing Group—http://www.nature.com./natureneuroscience—USA.

Huq et al.—Specific Recognition of HIV-1 TAR RNA by a D-Tat Peptide—Comment—Nature Structural Biology—Nov. 1997—pp. 881-882—vol. 4—No. 11—Nature Publishing Group—http://www.nature.com/nsmb—USA.

Inhibit.Dictionary.com—The American Heritage® Stedman's Medical Dictionary—Houghton Mifflin Company—One Page—Internet document: http://dictionary.reference.com/browse/inhibit—Accessed on Oct. 10, 2007—USA.

Jackson et al.—Heat Shock Induces the Release of Fibroblast Growth Factor 1 from NIH 3T3 Cells—Proceedings of National Academy of Sciences—Cell Biology—Nov. 1992—pp. 10691-10695—vol. 89—National Academy of Sciences—USA.

Kennedy, Norman J. and Davis, Roger J.—Perspectives: Role of JNK in Tumor Development—Cell Cycle—May/Jun. 2003—pp. 199-201—vol. 2—No. 3—www.landesbioscience.com—USA.

Kishan, K.V. Radha and Agrawal, Vishal—SH3-like Fold Proteins are Structurally Conserved and Functionally Divergent—Current Protein and Peptide Science—1995—pp. 143-150—vol. 6—Nentham Science Publishers Ltd.—USA.

Lebleu, Bernard—Delivering Information-Rich Drugs—Prospects and Challenges—Meeting Report—Apr. 1996—pp. 109-110—vol. 14—No. 4—Tibtech (Trends in Biotechnology) Elsevier Science Ltd.—USA.

Lee et al.—c-Jun N-terminal Kinasa (JNK) Mediates Feedback Inhibition of the Insulin Signaling Cascade—The Journal of Biological Chemistry—Jan. 31, 2003—pp. 2896-2902—vol. 278—No. 5—The American Society for Biochemistry and Molecular Biology, Inc.—USA.

Li, Shawn S.C.—Review Article—Specificity and Versatility of SH3 and Other Ptoline-Recognition Domains: Structural Basis and Implications for Cellular Signal Transduction—Biochemical Journal—Sep. 15, 2005—pp. 641-653—Biochemical Society—vol. 390—Part 3—United Kingdom.

Lin et al.—Inhibition of Nuclear Translocation of Transcription Factor NF-kappa B by a Synthetic Peptide Containing a Cell Membrane-Permeable Motif and Nuclear Localization Sequence—Journal of Biological Chemistry—Jun. 16, 1995—pp. 14255-14258—vol. 270—No. 24—The American Society for Biochemistry and Molecular Biology, Inc.—USA.

Mayer, Bruce J.—SH3 Domains: Complexity in Moderation—Commentary—Journal of Cell Science—Signal Transduction and Cellular Organization—Apr. 2001—pp. 1253-1263—vol. 114—The Company of Biologists Ltd—USA.

Messer, Jr., Dr. William S.—MBC 3320 Posterier Pituitary Hormones—Vasopression and Oxytocin—Apr. 3, 2000—pp. 1-5—,http://www.neurosci.pharm.utoledo.edu/MBC3320/vasopressin.htm>—USA.

Mooser et al.—Genomic Organization, Fine-Mapping, and Expression of the Human Islet-Brain 1 (IB1)/C-Jun-Amino-Terminal Kinase Interacting Protein-1 (JIP-1) Gene—Genomics—Jan. 15, 1999—pp. 202-208—vol. 55—Academic Press—USA.

Moulin, Nathalie and Widman, Christian—Islet-Brain (IB)/JNK-Interacting Proteins (JIPs): Future Targets for the Treatment of Neurodegenerative Diseases?—Current Neurovascular Research—2004—pp. 111-127—vol. 1—No. 2—Institut de Biologie Cellulaire et de Morphologie (IBCM)—Universite de Lusanne—Switzerland—Bentham Science Publishers Ltd.—USA.

Nagahara et al.—Transduction of Full-Length TAT Fusion Proteins into Mammalian Cells: TAT-p27Kip1 Induces Cell Migration—Nature Medicine—Dec. 1998—pp. 1449-1452—vol. 4—No. 12—Nature America Inc.—USA.

Ngo et al.—Computational Complexity, Protein Structure Prediction, and the Levinthal Paradox—The Protein Folding Problem and Tertiary Structure Prediction—Merz et al. (Editors)—1994—pp. 433, 492-495—Birkhauser Boston—USA.

Noguchi et al.—Regulation of c-Myc through Phosphorylation at Ser-62 and Ser-71 by c-Jun N-Terminal Kinase—Journal of Biological Chemistry—Nov. 12, 1999—pp. 32580-32587—vol. 274—No. 46—The American Society for Biochemistry and Molecular Biology, Inc.—USA.

Parkinson's Disease: Challenges, Progress, and Promise—Publication—National Institute of Neurological Disorders and Stroke—National Institutes of Health—2004—22 pages—No. 05-5595—<http://www.ninds.nih.gov/disorders/parkinsons_disease/parkinsons_research_pr.htm.

Mann et al, 1991, EMBO, pp. 1733-1739.

Marino et al., 1999, Eur. J. Immunology, 2560-2566.

Marks et al., 1996, JCB, pp. 341-354.

Mazur et al., 1999, J. Biol. Chem., pp. 19655-19660.

Melikov et al., 2005, CMLS Cellular and Molecular Life, pp. 2739-2749.

Mi et al., 2000, Molecular Therapy, pp. 339-347.

Milano Giuseppina et al., 2007, American Journal of Physiology, pp. H1828-H1835.
Mooi et al., 1986, NAR, pp. 2443-2457.
Moon et al., 2008, Cancer Letters, pp. 316-325.
Neundorf et al., 2008, Bioconjugate Chemistry, pp. 1596-1603.
Non et al, 2003, Bioconjugate Chemistry, pp. 44-50.
Nori et al, 2005, Advanced Drug Delivery Reviews, pp. 619-628.
Okitsu et al., 2003, Transplant. Proc., p. 479.
Pan Jing et al., 2010, Laboratory Investigation, pp. 156-167.
Penco et al, 2001, Biotechnology and Applied Biochenistry, pp. 151-159.
Peptide Science—Present and Future, pp. 782-787, 805-807.
Peptide Synthesis Protocols, 1994, pp. 201-239.
Peptide Synthesis Protocols, 1994, pp. 241-247.
Peptides 1996, pp. 447-451, 483-487.
Prantner et. al, 2003, Molecular Imaging Official Journal of the Society for Molecula.
Ramanathan et al, 2001, Pharmaceutical Research, pp. 950-956.
Ribeiro et al., 2003, Biochem. Biophys. Res. Comm., pp. 8769-8881.
Robinson et al., 2005, Bioorganic & Medicinal Chemistry, pp. 2055-2064.
Roy Praveen et al., 2008, World Journal of Gastroenterology, pp. 200-202.
Saito et al., 1997, Molecular Immunology, pp. 1133-1145.
Schimmer et al, 2001, Cell Death and Differentiation, pp. 725-733.
Schinzel et al., 1991, FEBS, pp. 125-128.
Sebestyen et al., 1998, Nat. Biotechnol., pp. 80-85.
Selective DImerisation of Cysteines to form Homodimers, 1997, NJE.
Stevens et al., 1998, Eur. J. Immunol, pp. 1272-1279.
Stevens et al., 1998, J. Biol. Chem., pp. 2874-2884.
Torchilin, 2005, Advanced Drug Delivery Reviews, pp. 95-109.
Zoukhri Driss et al., 2006, Journal of Neurochemistry, pp. 126-135.
Wadia et al., 2004, American Pharmaceutical Review 2004 United States, pp. 65-69.
Walsh et al, 2002, Blood, pp. 3439-3448.
Wender et al, 2000, Proceedings of the National Academy of Sciences of the United.
Whitmarsh et al., 1998, Science, pp. 1671-1674.
Wishart et al., 1995, Journal of Biological Chemistry, pp. 26782-26785.
Witkowski et al., 1999, Biochemistry, pp. 11643-11650.
Yamamoto et al., 2002, Current Drug Targets, pp. 123-130.

Peptides Sequences, Human, Mouse and Rat

A.

```
                    : :   **.:
IB2      :  IPSPSVEEPHKHRPTTLRL--TTLGAQDS   SEQ ID NO:18
IB1      :  PGTGCGDTYRPKRPTTLNLFPQVPRSQDT   SEQ ID NO:17
c-Jun    :  GAYGYSNPKILKQSMTLNLADPVGNLKPH   SEQ ID NO:19
ATF2     :  TNEDHLAVHKHKHEMTLKFGPARNDSVIV   SEQ ID NO:20
```

B.

```
            :  . .****** *      **:
L-IB2    :  EEPHKHRPTTLRL--TTLGAQDS   SEQ ID NO:2
L-IB1    :  DTYRPKRPTTLNLFPQVPRSQDT   SEQ ID NO:1
                           ° ° °
```

C.

```
L-TAT       :  NH2- GRKKRRQRRR -COOH                                          SEQ ID NO:7
L-TAT-IB1   :  NH2- GRKKRRQRRRPPDTYRPKRPTTLNLFPQVPRSQDT -COOH                 SEQ ID NO:11
L-TAT-IB2   :  NH2- GRKKRRQRRRPPEEPHKHRPTTLRLTTLGAQDS -COOH                   SEQ ID NO:12

D-TAT       :  NH2- RRRQRRKKRG -COOH                                          SEQ ID NO:8
D-TAT-IB1   :  NH2- TDQSRPVQPFLNLTTPRKPRYTDPPRRRQRRKKRG -COOH                 SEQ ID NO:14
```

Fig.1

Generic Sequences, Human, Mouse and Rat

| | | | |
|---|---|---|---|
| L-TAT-IB | : $NH_2$- XXXXXXXRKKRRQRRRXXXXXXXXXRPTTLXLXXXXXXXQDS/TX | -COOH | SEQ ID NO:13 |
| D-TAT | : $NH_2$- XXXXRRRQRRKKRXXXX -COOH | | SEQ ID NO:8 |
| D-TAT-IB | : $NH_2$- XT/SDQXXXXXXXLXLTTPRXXXXXXXXXRRRQRRKKRXXXXXXX | -COOH | SEQ ID NO:16 |

*Effects of GFP-JBD$_{23}$ Construct on Pancreatic β-Cell Apoptosis*

*Effects of TAT-IB Peptides on JNK Mediated Phosphorylation*

*Effects of TAT-IB Peptides on JNK Mediated Phosphorylation*

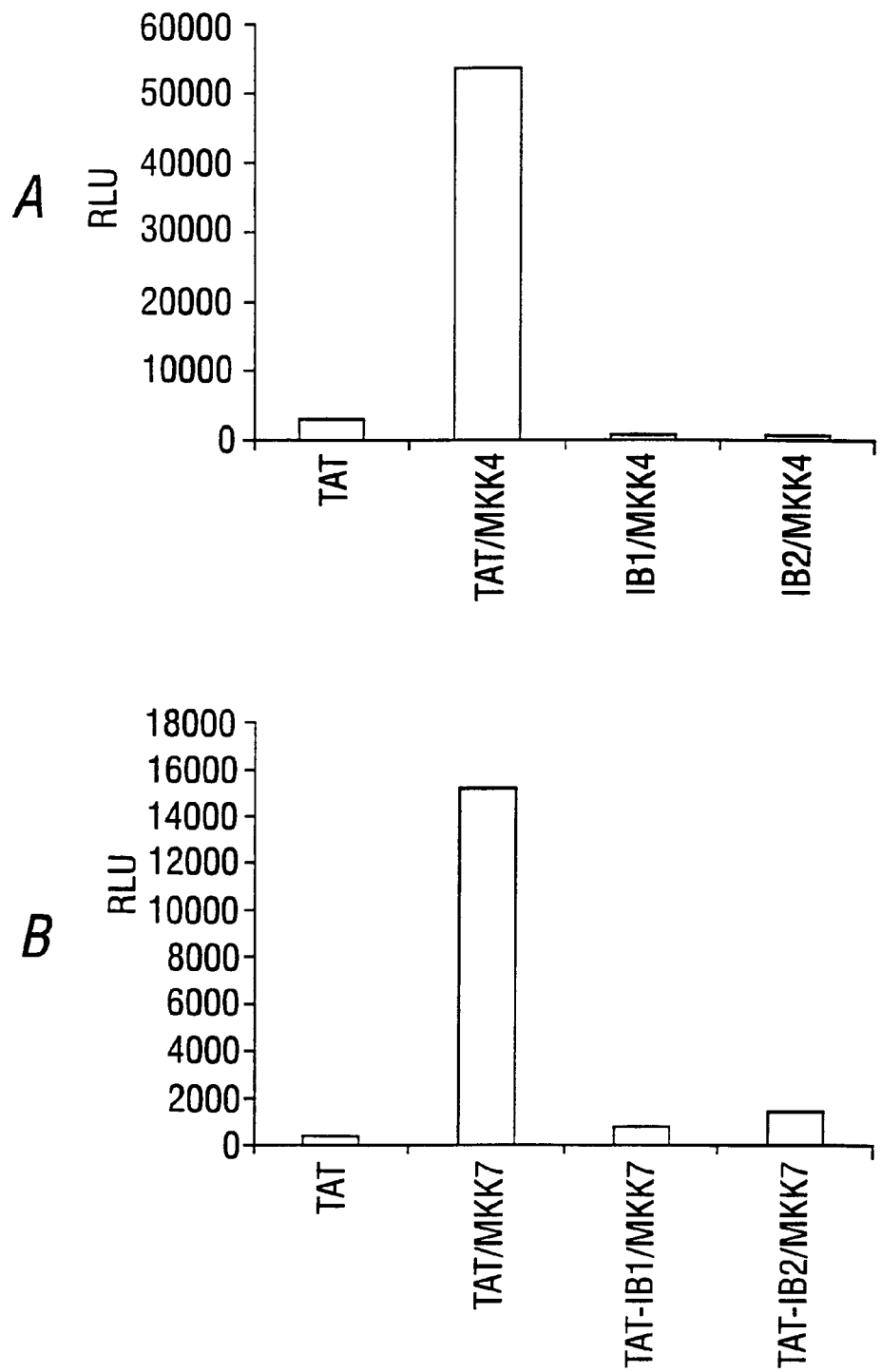
FIG. 5 L-TAT-IB Inhibition of Phosphorylation By Recombinant JNKs

*In Vivo Inhibition of c-Jun Phosphorylation by TAT-IB Peptides*

*Suppression of JNK Transcription Factor Phosphorylation by L-TAT-IB1 Peptides*

The D-TAT-IB1 peptide decreases IL-1-induced apoptosis in βTC-3 cells

Inhibition of IL-1β Induced Pancreatic β-Cell Death by TAT-IB Peptides

L-TAT-IB1 and D-TAT-IB1 peptides prevent IR-induced apoptosis in a human colon cancer cell line The D-TAT-IB1 peptide confers long-term protection (15 days) against IL-1-induced apoptosis in βTC-3 cells

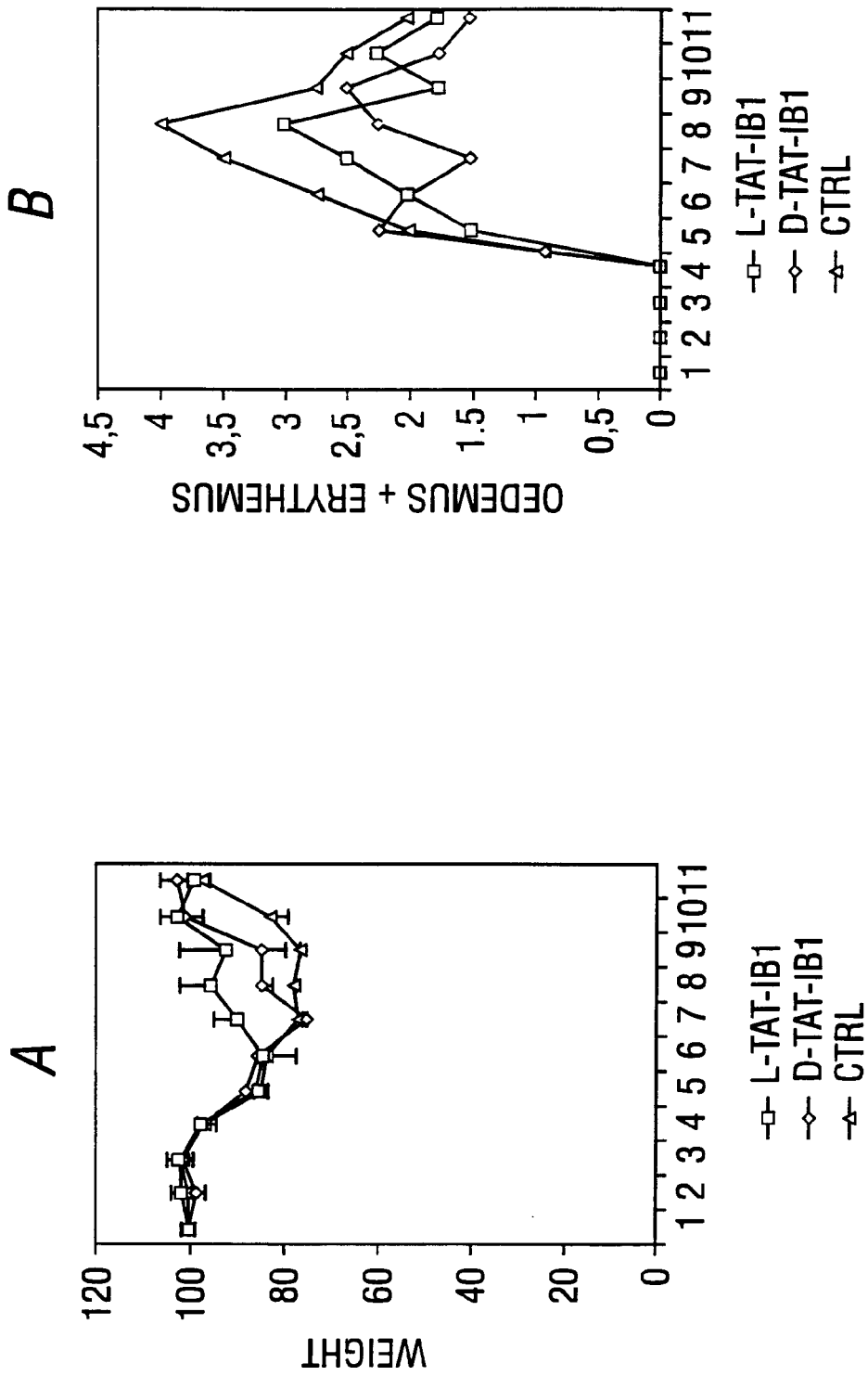
FIG. 12 Radioprotection to Ionizing Radiation by TAT-IB1 Peptides

CELL-PERMEABLE PEPTIDE INHIBITORS OF THE JNK SIGNAL TRANSDUCTION PATHWAY

RELATED APPLICATIONS

This application is a Divisional Application of U.S. patent application Ser. No. 10/110,430, filed Aug. 27, 2002, now U.S. Pat. No. 8,183,339 which is a National Stage Application, filed under U.S.C. §371 of International Application No. PCT/IB00/01538, with an international filing date of Oct. 12, 2000 and which is a Divisional Application of U.S. patent application Ser. No. 09/503,954, filed Feb. 14, 2000 (now U.S. Pat. No. 6,610,820) and U.S. Provisional Application No. 60/158,774, filed Oct. 12, 1999, all of which are incorporated herein by reference in their entireties.

FIELD OF THE INVENTION

This invention relates generally to protein kinase inhibitors and more specifically to inhibitors of the protein kinase c-Jun amino terminal kinase.

BACKGROUND OF THE INVENTION

The c-Jun amino terminal kinase (JNK) is a member of the stress-activated group of mitogen-activated protein (MAP) kinases. These kinases have been implicated in the control of cell growth and differentiation, and, more generally, in the response of cells to environmental stimuli. The JNK signal transduction pathway is activated in response to environmental stress and by the engagement of several classes of cell surface receptors. These receptors can include cytokine receptors, serpentine receptors, and receptor tyrosine kinases. In mammalian cells, JNK has been implicated in such biological processes as oncogenic transformation and in mediating adaptive responses to environmental stress. JNK has also been associated with modulating immune responses, including maturation and differentiation of immune cells, as well effecting programmed cell death in cells identified for destruction by the immune system.

SUMMARY OF THE INVENTION

The present invention is based in part on the discovery of peptides that are effective inhibitors of JNK proteins. The peptides, referred to herein as JNK peptide inhibitors, decrease the downstream cell-proliferative effects of c-Jun amino terminal kinase (JNK).

Accordingly, the invention includes novel JNK inhibitor peptides, as well as chimeric peptides which include a JNK peptide inhibitor linked a trafficking peptide that can be used to direct a peptide on which it is present do a desired cellular location. The trafficking sequence can be used to direct transport of the peptide across the plasma membrane. Alternatively, or in addition, the trafficking peptide can be used to direct the peptide to desired intracellular location, such as the nucleus.

The JNK inhibitor peptides can be present as polymers of L-amino acids. Alternatively, the peptides can be present as polymers of D-amino acids.

Also included in the invention are pharmaceutical compositions that include the JNK-binding peptides, as well as antibodies that specifically recognize the JNK-binding peptides.

The invention also includes a method of inhibiting expression of a JNK kinase in a cell.

In another aspect, the invention includes a method of treating a pathophysiology associated with activation of JNK in a cell or cells. For example, the target cells may be, e.g., cultured animal cells, human cells or micro-organisms. Delivery can be carried out in vivo by administering the chimeric peptide to an individual in whom it is to be used for diagnostic, preventative or therapeutic purposes. The target cells may be in vivo cells, i.e., cells composing the organs or tissues of living animals or humans, or microorganisms found in living animals or humans.

Among the advantages provided by the invention is that the JNK inhibitor peptides are small, and can be produced readily in bulk quantities and in high purity. The inhibitor peptides are also resistant to intracellular degradation, and are weakly immunogenic. Accordingly, the peptides are well suited for in vitro and in vivo applications in which inhibition of JNK-expression is desired.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIGS. 1A-C are diagrams showing alignments of conserved JBD domain regions in the indicated transcription factors. (SEQ ID NOS 18, 17, 19, 20, 2, 1, 7, 11, 12, 8 and 14, respectively in order of appearance)

FIG. 2 is a diagram showing alignments of generic TAT-IB fusion peptides. (SEQ ID NOS 13, 10 and 16, respectively, in order of appearance).

FIG. 5 is a histogram depicting L-TAT-IB inhibition of phosphorylation by recombinant JNKs. Panel A shows L-TAT-IB inhibition of c-Jun, ATF2 and Elk1 phosphorylation by recombinant JNKs in vitro in the presence of MKK4. Panel B shows similar dose response experiments with MKK7.

FIG. 12 are graphs depicting the protective effects of the TAT-IB1 peptides in mice. Panel A shows the effect of irradiation on weight. Panel B shows the effect of irradiation on oedemus and erythemus status.

DETAILED DESCRIPTION OF THE INVENTION

Figure 3:
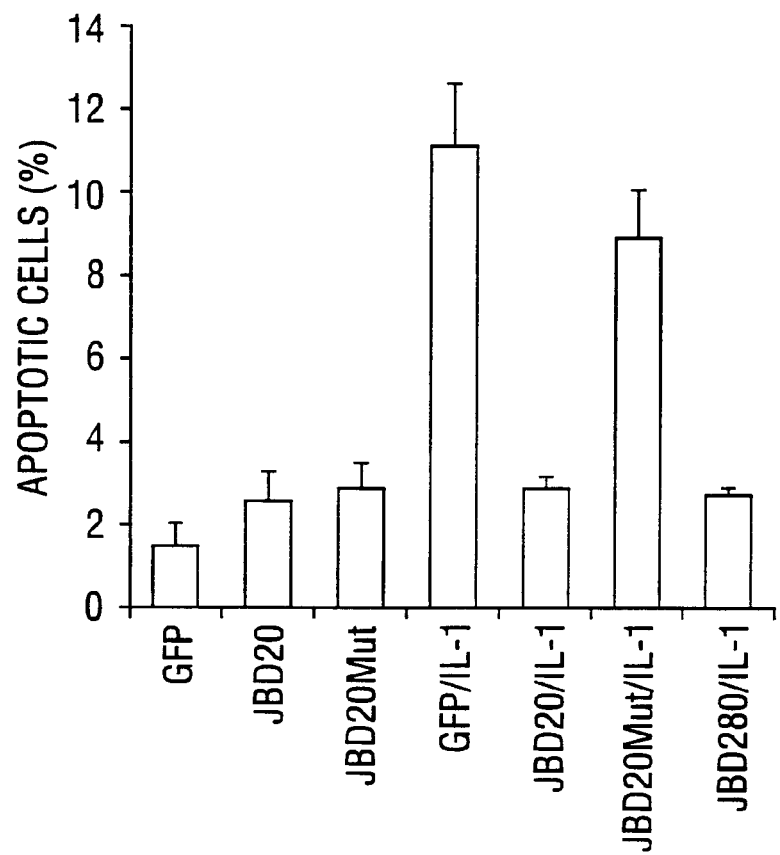
FIG. 3 is a histogram depicting inhibition of β-cell death by the minimal 23 amino acid long JBD domain of IB1 compared to the full 280 amino acid JBD domain.

The present invention is based in part on the discovery of cell permeable peptides that inhibit the activated c-Jun amino terminal kinase (JNK) signaling pathway. These peptides are referred to herein as JNK inhibitor peptides. Additionally, the discovery provides methods and pharmaceutical compositions for treating pathophysiologies associated with JNK signaling.

JNK inhibitor peptides were identified by inspecting sequence alignments between kJNK Binding Domains in various insulin binding (IB) proteins. The results of this alignment are shown in FIGS. 1A-1C. FIG. 1A depicts the region of highest homology between the JBDs of IB1, IB2, c-Jun and ATF2. Panel B depicts the amino acid sequence alignment of the JBDs of IB1 and IB2. Fully conserved residues are indicated by asterisks, while residues changed to Ala in the GFP-$JBD_{23Mut}$ vector are indicated by open circles. FIG. 1C shows the amino acid sequences of chimeric proteins that include a JNK inhibitor peptide domain and a trafficking domain. In the example shown, the trafficking domain is derived from the human immunodeficiency virus (HIV) TAT polypeptide, and the JNK inhibitor peptide is derived from an IB1 polypeptide. Human, mouse, and rat sequences are identical in Panels B and C.

Sequence comparison between the JNK binding domains of IB1 [SEQ ID NO: 17], IB2 [SEQ ID NO: 18], c-Jun [SEQ ID NO: 19] and ATF2 [SEQ ID NO: 20] revealed a partially conserved 8 amino acid sequence (FIG. 1A). A comparison of the JBDs of IB1 and IB2 further revealed two blocks of seven and three amino acids that are highly conserved between the two sequences. These two blocks are contained within a peptide sequence of 23 amino acids in IB1 [SEQ ID NO: 1] and 21 amino acids in IB2 [SEQ ID NO: 2].

The JNK inhibitor peptides of the invention can be used in any situation in which inhibition of JNK activity is desired. This can include in vitro applications, ex vivo, and in vivo applications. As JNKs and all its isoforms participate in the development and establishment of pathological states or in pathways, the JNK peptides can be used to prevent or inhibit the occurrence of such pathological states. This includes prevention and treatment of diseases and prevention and treatment of conditions secondary to therapeutic actions. For example, the peptides of the present invention can be used to treat or prevent, e.g., diabetes, ionizing radiation, immune responses (including autoimmune diseases), ischemia/reperfusion injuries, heart and cardiovascular hypertrophies, and some cancers (e.g., Bcr-Abl transformation).

The peptides can also be used to inhibit expression of genes whose expression increases in the presence of an active JNK polypeptide. These genes and gene products includes, e.g., proinflammatory cytokines. Such cytokines are found in all forms of inflammatory, auto-inflammatory, immune and autoimmune diseases, degenerative diseases, myopathies, cardiomyopathies, and graft rejection.

The JNK inhibitor peptides described herein can also be used to treat or prevent effects associated with cellular shear stress, such as in pathological states induced by arterial hypertension, including cardiac hypertrophy and arteriosclerotic lesions, and at bifurcations of blood vessels, and the like; ionizing radiation, as used in radiotherapy and UV lights; free radicals; DNA damaging agents, including chemotherapeutic drugs; oncogenic transformation; ischemia and reperfusion; hypoxia; and hypo- and hyperthermia.

The polynucleotides provided by the present invention can be used to express recombinant peptides for analysis, characterization or therapeutic use; as markers for tissues in which the corresponding peptides is preferentially expressed (either constitutively or at a particular stage of tissue differentiation or development or in disease states). Other uses for the nucleic acids include, e.g., molecular weight markers in gel electrophoresis-based analysis of nucleic acids.

The JNK inhibitor peptides disclosed herein are presented in Table 1. The table presents the name of the JNK inhibitor peptide, as well as its sequence identifier number, length, and amino acid sequence.

TABLE 1

| PEPTIDE NAME | SEQ ID | AA | Sequence |
|---|---|---|---|
| L-IB1 | 1 | 23 | DTYRPKRPTT LNLFPQVPRS QDT |
| L-IB2 | 2 | 21 | EEPHKHRPTT LRLTTLGAQD S |
| D-IB1 | 3 | 23 | TDQSRPVQPF LNLTTPRKPR YTD |
| D-IB2 | 4 | 21 | SDQAGLTTLR LTTPRHKHPE E |
| L-IB (generic) | 5 | 19 | XRPTTLXLXX XXXXXQDS/TX |
| D-IB (generic) | 6 | 19 | XS/TDQXXXXXX XLXLTTPRX |
| L-TAT | 7 | 10 | GRKKRRQRRR |
| D-TAT | 8 | 10 | RRRQRRKKRG |
| L-generic-TAT | 9 | 17 | XXXXRKKRRQ RRRXXXX |
| D-generic-TAT | 10 | 17 | XXXXRRRQRR KKRXXXX |
| L-TAT-IB1 | 11 | 35 | GRKKRRQRRR PPDTYRPKRP TTLNLFPQVP RSQDT |

TABLE 1-continued

| PEPTIDE NAME | SEQ ID | AA Sequence |
| --- | --- | --- |
| L-TAT-IB2 | 12 | 33 GRKKRRQRRR PPEEPHKHRP TTLRLTTLGA QDS |
| L-TAT-IB (generic) | 13 | 42 XXXXXXXRKK RRQRRRXXXX XXXXRPTTLX LXXXXXXXQD S/TX |
| D-TAT-IB1 | 14 | 35 TDQSRPVQPF LNLTTPRKPR YTDPPRRRQR RKKRG |
| D-TAT-IB2 | 15 | 33 SDQAGLTTLR LTTPRHKHPE EPPRRRQRRK KRG |
| D-TAT-IB (generic) | 16 | 42 XT/SDQXXXXXX XLXLTTPRXX XXXXXXRRRQ RRKKRXXXX XX |
| IB1-long | 17 | 29 PGTGCGDTYR PKRPTTLNLF PQVPRSQDT |
| IB2-long | 18 | 27 IPSPSVEEPH KHRPTTLRLT TLGAQDS |
| c-Jun | 19 | 29 GAYGYSNPKI LKQSMTLNLA DPVGNLKPH |
| ATF2 | 20 | 29 TNEDHLAVHK HKHEMTLKFG PARNDSVIV |

JNK Inhibitor Peptides

In one aspect, the invention provides a JNK inhibitor peptide. No particular length is implied by the term "peptide." In some embodiments, the JNK-inhibitor peptide is less than 280 amino acids in length, e.g., less than or equal to 150, 100, 75, 50, 35, or 25 amino acids in length. In various embodiment, the JNK-binding inhibitor peptide includes the amino acid sequence of one or more of SEQ ID NOs: 1-6. In one embodiment, the JNK inhibitor peptide peptides bind JNK. In another embodiment the peptide inhibits the activation of at least one JNK activated transcription factor, e.g. c-Jun, ATF2 or Elk1.

Examples of JNK inhibitor peptides include a peptide which includes (in whole or in part) the sequence NH$_2$-DTYRPKRPTTLNLFPQVPRSQDT-COOH [SEQ ID NO:1]. In another embodiment, the peptide includes the sequence NH$_2$-EEPHKHRPTTLRLTTLGAQDS-COOH [SEQ ID NO:2]

The JNK inhibitor peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., *Nature,* 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into an D retro-inverso peptide by synthesizing a reverse of the sequence for the corresponding native L-amino acid sequence.

In one embodiment, a D retro-inverso peptide has the sequence NH$_2$-TDQSRPVQPFLNLTTPRKPRYTD-COOH [SEQ ID NO:3]. In another embodiment the D retro-inverso peptide has the sequence NH$_2$-SDQAGLTTLRLTTPRHKH-PEE-COOH [SEQ ID NO: 4]. It has been unexpectedly found that D-retro-inverso TAT-IB peptides have a variety of useful properties. For example, D-TAT and D-TAT-IB peptides enter cells as efficiently as L-TAT and L-TAT-IB peptides, and D-TAT and D-TAT-IB peptides are more stable than the corresponding L-peptides. Further, while D-TAT-IB1 are ~10-20 fold less efficient in inhibiting JNK than L-TAT-IB, they are ~50 fold more stable in vivo. Finally, as is discussed further below, D-TAT-IB peptides protect interleukin-1 treated and ionizing irradiated cells from apoptosis.

In another embodiment, a JNK inhibitor peptide according to the invention includes the amino acid sequence NH$_2$-XRPTTLXLXXXXXXXQDS/TX-COOH [SEQ ID NO: 5, and residues 24-42 of L-TAT-IB, SEQ ID NO: 13, as shown in FIG. 2]. As used herein, X may be zero or one residue in length. The single residue represented by S/T may be either Ser or Thr in the generic sequence. In a further embodiment, the generic IB peptide may be a D retro-inverso peptide having the sequence NH$_2$-XS/TDQXXXXXXXLXLT-TPRX-COOH [SEQ ID NO: 6, and residues 1-19 of D-TAT-IB, SEQ ID NO:16, as shown in FIG. 2].

JNK-inhibitor peptides may be obtained or produced by methods well-known in the art, e.g. chemical synthesis, genetic engineering methods as discussed below. For example, a peptide corresponding to a portion of a JNK inhibitor peptide including a desired region or domain, or that mediates the desired activity in vitro, may be synthesized by use of a peptide synthesizer.

A candidate JNK inhibitor peptide may also be analyzed by hydrophilicity analysis (see, e.g., Hopp and Woods, 1981. *Proc Natl Acad Sci USA* 78: 3824-3828) that can be utilized to identify the hydrophobic and hydrophilic regions of the peptides, thus aiding in the design of substrates for experimental manipulation, such as in binding experiments, antibody synthesis. Secondary structural analysis may also be performed to identify regions of a JNK inhibitor peptide that assume specific structural motifs. See e.g., Chou and Fasman, 1974. *Biochem* 13: 222-223. Manipulation, translation, secondary structure prediction, hydrophilicity and hydrophobicity profiles, open reading frame prediction and plotting, and determination of sequence homologies can be accomplished using computer software programs available in the art. Other methods of structural analysis including, e.g., X-ray crystallography (see, e.g., Engstrom, 1974. *Biochem Exp Biol* 11: 7-13); mass spectroscopy and gas chromatography (see, e.g., METHODS IN PROTEIN SCIENCE, 1997. J. Wiley and Sons, New York, N.Y.) and computer modeling (see, e.g., Fletterick and Zoller, eds., 1986. Computer Graphics and Molecular Modeling, In: CURRENT COMMUNICATIONS IN MOLECULAR BIOLOGY, Cold Spring Harbor Laboratory Press, Cold Spring Harbor, N.Y.) may also be employed.

The present invention additionally relates to nucleic acids that encode JNK-binding peptides having L-form amino acids, e.g., those L-peptides indicated in Table 1, as well as the complements of these sequences. Suitable sources of nucleic acids encoding JNK inhibitor peptides include the human IB1 nucleic acid (and the encoded protein sequences) available as GenBank Accession Nos. AF074091 and AAD20443, respectively. Other sources include rat IB1 nucleic acid and protein sequences are shown in GenBank Accession No. AF108959 and AAD22543, respectively, and are incorporated herein by reference in their entirety. Human IB2 nucleic acid and protein sequences are shown in Gen-Bank Accession No AF218778 and is also incorporated herein by reference in their entirety.

Nucleic acids encoding the JNK inhibitor peptides may be obtained by any method known in the art (e.g., by PCR amplification using synthetic primers hybridizable to the 3'- and 5'-termini of the sequence and/or by cloning from a cDNA or genomic library using an oligonucleotide sequence specific for the given gene sequence).

For recombinant expression of one or more JNK inhibitor peptides, the nucleic acid containing all or a portion of the nucleotide sequence encoding the peptide may be inserted into an appropriate expression vector (i.e., a vector that contains the necessary elements for the transcription and translation of the inserted peptide coding sequence). In some embodiments, the regulatory elements are heterologous (i.e., not the native gene promoter). Alternately, the necessary transcriptional and translational signals may also be supplied by the native promoter for the genes and/or their flanking regions.

A variety of host-vector systems may be utilized to express the peptide coding sequence(s). These include, but are not limited to: (i) mammalian cell systems that are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

Promoter/enhancer sequences within expression vectors may utilize plant, animal, insect, or fungus regulatory sequences, as provided in the invention. For example, promoter/enhancer elements can be used from yeast and other fungi (e.g., the GAL4 promoter, the alcohol dehydrogenase promoter, the phosphoglycerol kinase promoter, the alkaline phosphatase promoter). Alternatively, or in addition, they may include animal transcriptional control regions, e.g., (i) the insulin gene control region active within pancreatic β-cells (see, e.g., Hanahan, et al., 1985. *Nature* 315: 115-122); (ii) the immunoglobulin gene control region active within lymphoid cells (see, e.g., Grosschedl, et al., 1984. *Cell* 38: 647-658); (iii) the albumin gene control region active within liver (see, e.g., Pinckert, et al., 1987. *Genes and Dev* 1: 268-276; (iv) the myelin basic protein gene control region active within brain oligodendrocyte cells (see, e.g., Readhead, et al., 1987. *Cell* 48: 703-712); and (v) the gonadotropin-releasing hormone gene control region active within the hypothalamus (see, e.g., Mason, et al., 1986. *Science* 234: 1372-1378), and the like.

Expression vectors or their derivatives include, e.g. human or animal viruses (e.g., vaccinia virus or adenovirus); insect viruses (e.g., baculovirus); yeast vectors; bacteriophage vectors (e.g., lambda phage); plasmid vectors and cosmid vectors.

A host cell strain may be selected that modulates the expression of inserted sequences of interest, or modifies or processes expressed peptides encoded by the sequences in the specific manner desired. In addition, expression from certain promoters may be enhanced in the presence of certain inducers in a selected host strain; thus facilitating control of the expression of a genetically-engineered peptides. Moreover, different host cells possess characteristic and specific mechanisms for the translational and post-translational processing and modification (e.g., glycosylation, phosphorylation, and the like) of expressed peptides. Appropriate cell lines or host systems may thus be chosen to ensure the desired modification and processing of the foreign peptide is achieved. For example, peptide expression within a bacterial system can be used to produce an unglycosylated core peptide; whereas expression within mammalian cells ensures "native" glycosylation of a heterologous peptide.

Also included in the invention are derivatives, fragments, homologs, analogs and variants of JNK inhibitor peptides and nucleic acids encoding these peptides. For nucleic acids, derivatives, fragments, and analogs provided herein are defined as sequences of at least 6 (contiguous) nucleic acids, and which have a length sufficient to allow for specific hybridization. For amino acids, derivatives, fragments, and analogs provided herein are defined as sequences of at least 4 (contiguous) amino acids, a length sufficient to allow for specific recognition of an epitope.

The length of the fragments are less than the length of the corresponding full-length nucleic acid or polypeptide from which the JNK inhibitor peptide, or nucleic acid encoding same, is derived. Derivatives and analogs may be full length or other than full length, if the derivative or analog contains a modified nucleic acid or amino acid. Derivatives or analogs of the JNK inhibitor peptides include, e.g., molecules including regions that are substantially homologous to the peptides, in various embodiments, by at least about 30%, 50%, 70%, 80%, or 95%, 98%, or even 99%, identity over an amino acid sequence of identical size or when compared to an aligned sequence in which the alignment is done by a computer homology program known in the art. For example sequence identity can be measured using sequence analysis software (Sequence Analysis Software Package of the Genetics Computer Group, University of Wisconsin Biotechnology Center, 1710 University Avenue, Madison, Wis. 53705), with the default parameters therein.

In the case of polypeptide sequences, which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Thus, included in the invention are peptides having mutated sequences such that they remain homologous, e.g. in sequence, in function, and in antigenic character or other function, with a protein having the corresponding parent sequence. Such mutations can, for example, be mutations involving conservative amino acid changes, e.g., changes between amino acids of broadly similar molecular properties. For example, interchanges within the aliphatic group alanine, valine, leucine and isoleucine can be considered as conservative. Sometimes substitution of glycine for one of these can also be considered conservative. Other conservative interchanges include those within the aliphatic group aspartate and glutamate; within the amide group asparagine and glutamine; within the hydroxyl group serine and threonine; within the aromatic group phenylalanine, tyrosine and tryptophan; within the basic group lysine, arginine and histidine; and within the sulfur-containing group methionine and cysteine. Sometimes substitution within the group methionine and leucine can also be considered conservative. Preferred conservative substitution groups are aspartate-glutamate; asparagine-glutamine; valine-leucine-isoleucine; alanine-valine; phenylalanine-tyrosine; and lysine-arginine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide, which is 50% identical to the reference polypeptide over its entire length. Of course, other polypeptides will meet the same criteria.

The invention also encompasses allelic variants of the disclosed polynucleotides or peptides; that is, naturally-occurring alternative forms of the isolated polynucleotide that also encode peptides that are identical, homologous or related to that encoded by the polynucleotides. Alternatively, non-naturally occurring variants may be produced by mutagenesis techniques or by direct synthesis.

Species homologs of the disclosed polynucleotides and peptides are also provided by the present invention. "Variant" refers to a polynucleotide or polypeptide differing from the polynucleotide or polypeptide of the present invention, but retaining essential properties thereof. Generally, variants are overall closely similar, and in many regions, identical to the polynucleotide or polypeptide of the present invention. The variants may contain alterations in the coding regions, non-coding regions, or both.

In some embodiments, altered sequences include insertions such that the overall amino acid sequence is lengthened while the protein retains trafficking properties. Additionally, altered sequences may include random or designed internal deletions that shorten the overall amino acid sequence while the protein retains transport properties.

The altered sequences can additionally or alternatively be encoded by polynucleotides that hybridize under stringent conditions with the appropriate strand of the naturally-occurring polynucleotide encoding a polypeptide or peptide from which the JNK inhibitor peptide is derived. The variant peptide can be tested for JNK-binding and modulation of JNK-mediated activity using the herein described assays. 'Stringent conditions' are sequence dependent and will be different in different circumstances. Generally, stringent conditions can be selected to be about 5° C. lower than the thermal melting point ($T_M$) for the specific sequence at a defined ionic strength and pH. The $T_M$ is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may affect the stringency of hybridization (including, among others, base composition and size of the complementary strands), the presence of organic solvents and the extent of base mismatching, the combination of parameters is more important than the absolute measure of any one.

High stringency can include, e.g., Step 1: Filters containing DNA are pretreated for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Step 2: Filters are hybridized for 48 hours at 65° C. in the above prehybridization mixture to which is added 100 mg/ml denatured salmon sperm DNA and 5-20×$10^6$ cpm of $^{32}$P-labeled probe. Step 3: Filters are washed for 1 hour at 37° C. in a solution containing 2×SSC, 0.01% PVP, 0.01% Ficoll, and 0.01% BSA. This is followed by a wash in 0.1×SSC at 50° C. for 45 minutes. Step 4: Filters are autoradiographed. Other conditions of high stringency that may be used are well known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Moderate stringency conditions can include the following: Step 1: Filters containing DNA are pretreated for 6 hours at 55° C. in a solution containing 6×SSC, 5×Denhardt's solution, 0.5% SDS and 100 mg/ml denatured salmon sperm DNA. Step 2: Filters are hybridized for 18-20 hours at 55° C. in the same solution with 5-20×106 cpm $^{32}$P-labeled probe added. Step 3: Filters are washed at 37° C. for 1 hour in a solution containing 2×SSC, 0.1% SDS, then washed twice for 30 minutes at 60° C. in a solution containing 1×SSC and 0.1% SDS. Step 4: Filters are blotted dry and exposed for autoradiography. Other conditions of moderate stringency that may be used are well-known in the art. See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Low stringency can include: Step 1: Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Step 2: Filters are hybridized for 18-20 hours at 40° C. in the same solution with the addition of 0.02% PVP, 0.02% Ficoll, 0.2% BSA, 100 µg/ml salmon sperm DNA, 10% (wt/vol) dextran sulfate, and 5-20× 106 cpm $^{32}$P-labeled probe. Step 3: Filters are washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours at 60° C. Step 4: Filters are blotted dry and exposed for autoradiography. If necessary, filters are washed for a third time at 65-68° C. and reexposed to film. Other conditions of low stringency that may be used are well known in the art (e.g., as employed for cross-species hybridizations). See, e.g., Ausubel et al., (eds.), 1993, CURRENT PROTOCOLS IN MOLECULAR BIOLOGY, John Wiley and Sons, NY; and Kriegler, 1990, GENE TRANSFER AND EXPRESSION, A LABORATORY MANUAL, Stockton Press, NY.

Chimeric Peptides Including a JNK Inhibitor Domain and a Trafficking Domain

In another aspect the invention provides a chimeric peptide that includes a first and second domain. The first domain includes a trafficking sequence, while the second domain includes a JNK inhibitor sequence linked by a covalent bond, e.g. peptide bond, to the first domain. The first and second domains can occur in any order in the peptide, and the peptide can include one or more of each domain.

A trafficking sequence is any sequence of amino acids that directs a peptide in which it is present to a desired cellular destination. Thus, the trafficking sequence can direct the peptide across the plasma membrane, e.g., from outside the cell, through the plasma membrane, and into the cytoplasm. Alternatively, or in addition, the trafficking sequence can direct the peptide to a desired location within the cell, e.g., the nucleus, the ribosome, the ER, a lysosome, or peroxisome.

In some embodiments, the trafficking peptide is derived from a known membrane-translocating sequence. For example, the trafficking peptide may include sequences from the human immunodeficiency virus (HIV)1 TAT protein. This protein is described in, e.g., U.S. Pat. Nos. 5,804,604 and 5,674,980, each incorporated herein by reference. The JNK inhibitor peptide may be linked to some or all of the entire 86 amino acids that make up the TAT protein. For example, a functionally effective fragment or portion of a TAT protein that has fewer than 86 amino acids, which exhibits uptake into cells, and optionally uptake into the cell nucleus, can be used. In one embodiment, the fragment includes a peptide containing TAT residues 48-57, e.g. $NH_2$-GRKKRRQRRR-COOH [SEQ ID NO: 7] or a generic TAT sequence $NH_2$-XRKKRRQRRRX-COOH [SEQ ID NO: 9]. A TAT peptide that includes the region that mediates entry and uptake into cells can be further defined using known techniques. See, e.g., Franked et al., *Proc. Natl. Acad. Sci, USA* 86: 7397-7401 (1989).

The TAT sequence may be linked either to the N-terminal or the C-terminal end of JNK inhibitor sequence. A hinge of two proline residues may be added between the TAT and JNK inhibitor peptide to create the full fusion peptide. For example, L-amino acid fusion peptides may be the L-TAT-IB1 peptide [SEQ ID NO:11], the L-TAT-IB2 peptide [SEQ ID NO:12], or the generic L-TAT-IB peptide [SEQ ID NO:13]. D retro-inverso fusion peptides may be the D-TAT-IB1 peptide [SEQ ID NO:14], the D-TAT-IB2 peptide [SEQ ID NO:15], or the generic D-TAT-IB peptide [SEQ ID NO:16]. The TAT peptide may be a D retro-inverso peptide having the sequence $NH_2$-XRRRQRRKKRX-COOH [SEQ ID NO:10]. In SEQ ID NOs:5-6, 9-10, 13 and 16, the number of "X" residues is not limited to the one depicted, and may vary as described above.

The trafficking sequence can be a single (i.e., continuous) amino acid sequence present in the TAT sequence. Alternatively it can be two or more amino acid sequences, which are present in TAT protein, but in the naturally-occurring protein are separated by other amino acid sequences. As used herein, TAT protein includes a naturally-occurring amino acid sequence that is the same as that of naturally-occurring TAT protein, or its functional equivalent protein or functionally equivalent fragments thereof (peptides). Such functional equivalent proteins or functionally equivalent fragments possess uptake activity into the cell and into the cell nucleus that is substantially similar to that of naturally-occurring TAT protein. TAT protein can be obtained from naturally-occurring sources or can be produced using genetic engineering techniques or chemical synthesis.

The amino acid sequence of naturally-occurring HIV TAT protein can be modified, for example, by addition, deletion and/or substitution of at least one amino acid present in the naturally-occurring TAT protein, to produce modified TAT protein (also referred to herein as TAT protein). Modified TAT protein or TAT peptide analogs with increased or decreased stability can be produced using known techniques. In some embodiments TAT proteins or peptides include amino acid sequences that are substantially similar, although not identical, to that of naturally-occurring TAT protein or portions thereof. In addition, cholesterol or other lipid derivatives can be added to TAT protein to produce a modified TAT having increased membrane solubility.

Variants of the TAT protein can be designed to modulate intracellular localization of TAT-JNK inhibitor peptide. When added exogenously, such variants are designed such that the ability of TAT to enter cells is retained (i.e., the uptake of the variant TAT protein or peptide into the cell is substantially similar to that of naturally-occurring HIV TAT). For example, alteration of the basic region thought to be important for nuclear localization (see, e.g., Dang and Lee, *J. Biol. Chem.* 264: 18019-18023 (1989); Hauber et al., *J. Virol.* 63: 1181-1187 (1989); Ruben et al., *J. Virol.* 63: 1-8 (1989)) can result in a cytoplasmic location or partially cytoplasmic location of TAT, and therefore, of the JNK inhibitor peptide. Alternatively, a sequence for binding a cytoplasmic or any other component or compartment (e.g., endoplasmic reticule, mitochondria, gloom apparatus, lysosomal vesicles,) can be introduced into TAT in order to retain TAT and the JNK inhibitor peptide in the cytoplasm or any other compartment to confer regulation upon uptake of TAT and the JNK inhibitor peptide.

Other sources for the trafficking peptide include, e.g., VP22 (described in, e.g., WO 97/05265; Elliott and O'Hare, *Cell* 88: 223-233 (1997)), or non-viral proteins (Jackson et al, *Proc. Natl. Acad. Sci. USA* 89: 10691-10695 (1992)).

The JNK inhibitor sequence and the trafficking sequence can be linked by chemical coupling in any suitable manner known in the art. Many known chemical cross-linking methods are non-specific, i.e.; they do not direct the point of coupling to any particular site on the transport polypeptide or cargo macromolecule. As a result, use of non-specific cross-linking agents may attack functional sites or sterically block active sites, rendering the conjugated proteins biologically inactive.

One way to increasing coupling specificity is to directly chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

Cysteine residues may be replaced when they occur in parts of a polypeptide sequence where their participation in a cross-linking reaction would otherwise likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized, See for example, Means and Feeney, CHEMICAL MODIFICATION OF PROTEINS, Holden-Day, 1974, pp. 39-43. Among these reagents are, for example, J-succinimidyl 3-(2-pyridyldithio)propionate (SPDP) or N,N'-(1,3-phenylene)bismaleimide (both of which are highly specific for sulfhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m,m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, Traut's reagent, dithiobis(succinimidylpropionate) ("DSP"), and N-succinimidyl 3-(2-pyridyldithio)propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Numerous cross-linking reagents, including the ones discussed above, are commercially available. Detailed instructions for their use are readily available from the commercial suppliers. A general reference on protein cross-linking and conjugate preparation is: Wong, CHEMISTRY OF PROTEIN CONJUGATION AND CROSS-LINKING, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety that includes spacer amino acids, e.g. proline. Alternatively, a spacer arm may be part of the cross-linking reagent, such as in "long-chain SPDP" (Pierce Chem. Co., Rockford, Ill., cat. No. 21651 H).

Alternatively, the chimeric peptide can be produced as a fusion peptide that includes the trafficking sequence and the JNK inhibitor sequence which can conveniently be expressed in known suitable host cells. Fusion peptides, as described herein, can be formed and used in ways analogous to or readily adaptable from standard recombinant DNA techniques, as describe above.

Production of Antibodies Specific for JNK Inhibitor Peptides

JNK inhibitor peptides, including chimeric peptides including the JNK inhibitor peptides (e.g., peptides including the amino acid sequences shown in Table 1), as well peptides, or derivatives, fragments, analogs or homologs thereof, may be utilized as immunogens to generate antibodies that immunospecifically-bind these peptide components. Such antibodies include, e.g., polyclonal, monoclonal, chimeric, single chain, Fab fragments and a Fab expression library. In a specific embodiment, antibodies to human peptides are disclosed. In another specific embodiment, fragments of the JNK inhibitor peptides are used as immunogens for antibody production. Various procedures known within the art may be used for the production of polyclonal or monoclonal antibodies to a JNK inhibitor peptide, or derivative, fragment, analog or homolog thereof.

For the production of polyclonal antibodies, various host animals may be immunized by injection with the native peptide, or a synthetic variant thereof, or a derivative of the foregoing. Various adjuvants may be used to increase the immunological response and include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.) and human adjuvants such as Bacille Calmette-Guerin and *Corynebacterium parvum*.

For preparation of monoclonal antibodies directed towards a JNK inhibitor peptide, or derivatives, fragments, analogs or homologs thereof, any technique that provides for the production of antibody molecules by continuous cell line culture may be utilized. Such techniques include, but are not limited to, the hybridoma technique (see, Kohler and Milstein, 1975. *Nature* 256: 495-497); the trioma technique; the human B-cell hybridoma technique (see, Kozbor, et al., 1983. *Immunol Today* 4: 72) and the EBV hybridoma technique to produce human monoclonal antibodies (see, Cole, et al., 1985. In: *Monoclonal Antibodies and Cancer Therapy*, Alan R. Liss, Inc., pp. 77-96). Human monoclonal antibodies may be utilized in the practice of the present invention and may be produced by the use of human hybridomas (see, Cote, et al., 1983. *Proc Natl Acad Sci USA* 80: 2026-2030) or by transforming human B-cells with Epstein Barr Virus in vitro (see, Cole, et al., 1985. In: *Monoclonal Antibodies and Cancer Therapy* (Alan R. Liss, Inc., pp. 77-96).

According to the invention, techniques can be adapted for the production of single-chain antibodies specific to a JNK inhibitor peptide (see, e.g., U.S. Pat. No. 4,946,778). In addition, methodologies can be adapted for the construction of Fab expression libraries (see, e.g., Huse, et al., 1989. *Science* 246: 1275-1281) to allow rapid and effective identification of monoclonal Fab fragments with the desired specificity for a JNK inhibitor peptide or derivatives, fragments, analogs or homologs thereof. Non-human antibodies can be "humanized" by techniques well known in the art. See e.g., U.S. Pat. No. 5,225,539. Antibody fragments that contain the idiotypes to a JNK inhibitor peptide may be produced by techniques known in the art including, e.g., (i) an $F(ab')_2$ fragment produced by pepsin digestion of an antibody molecule; (ii) an Fab fragment generated by reducing the disulfide bridges of an $F(ab')_2$ fragment; (iii) an Fab fragment generated by the treatment of the antibody molecule with papain and a reducing agent and (iv) Fv fragments.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a JNK inhibitor peptide is facilitated by generation of hybridomas that bind to the fragment of a JNK inhibitor peptide possessing such a domain. Antibodies that are specific for a domain within a JNK inhibitor peptide, or derivative, fragments, analogs or homologs thereof, are also provided herein.

The anti-JNK inhibitor peptide antibodies may be used in methods known within the art relating to the localization and/or quantitation of a JNK inhibitor peptide (e.g., for use in measuring levels of the peptide within appropriate physiological samples, for use in diagnostic methods, for use in imaging the peptide, and the like). In a given embodiment, antibodies for the JNK inhibitor peptides, or derivatives, fragments, analogs or homologs thereof that contain the antibody derived binding domain, are utilized as pharmacologically active compounds [hereinafter "Therapeutics"].

Methods of Treating or Preventing Disorders Associated Undesired JNK Activity

Also included in the invention also are methods of treating cell-proliferative disorders associated with JNK activation in a subject by administering to a subject a biologically-active therapeutic compound (hereinafter "Therapeutic"). The subject can be e.g., any mammal, e.g., a human, a primate, mouse, rat, dog, cat, cow, horse, pig.

The Therapeutics include, e.g.: (i) any one or more of the JNK inhibitor peptides, and derivative, fragments, analogs and homologs thereof; (ii) antibodies directed against the JNK inhibitor peptides; (iii) nucleic acids encoding a JNK inhibitor peptide, and derivatives, fragments, analogs and homologs thereof; (iv) antisense nucleic acids to sequences encoding a JNK inhibitor peptide, and (v) modulators (i.e., inhibitors, agonists and antagonists).

The term "therapeutically effective" means that the amount of inhibitor peptide, for example, which is used, is of sufficient quantity to ameliorate the JNK associated disorder. The term "cell-proliferative disorder" denotes malignant as well as non-malignant cell populations that often appear to differ morphologically and functionally from the surrounding tissue. For example, the method may be useful in treating malignancies of the various organ systems, in which activation of JNK has often been demonstrated, e.g., lung, breast, lymphoid, gastrointestinal, and genito-urinary tract as well as adenocarcinomas which include malignancies such as most colon cancers, renal-cell carcinoma, prostate cancer, non-small cell carcinoma of the lung, cancer of the small intestine and cancer of the esophagus. Cancers with Bcr-Abl oncogenic transformations that clearly require activation of JNK are also included.

The method is also useful in treating non-malignant or immunological-related cell-proliferative diseases such as psoriasis, pemphigus vulgaris, Behcet's syndrome, acute respiratory distress syndrome (ARDS), ischemic heart disease, post-dialysis syndrome, leukemia, rheumatoid arthritis, acquired immune deficiency syndrome, vasculitis, septic shock and other types of acute inflammation, and lipid histiocytosis. Especially preferred are immunopathological disorders. Essentially, any disorder, which is etiologically linked to JNK kinase activity, would be considered susceptible to treatment.

Treatment includes administration of a reagent that modulates JNK kinase activity. The term "modulate" includes the suppression of expression of JNK when it is over-expressed. It also includes suppression of phosphorylation of c-jun, ATF2 or NFAT4, for example, by using a peptide of any one or more of SEQ ID NOs: 1-6 and SEQ ID NOs: 11-16 as a competitive inhibitor of the natural c-jun ATF2 and NFAT4 binding site in a cell. Thus also includes suppression of hetero- and homo-meric complexes of transcription factors made up of c-jun, ATF2, or NFAT4 and their related partners, such as for example the AP-1 complex that is made up of c-jun, AFT2 and c-fos. When a cell proliferative disorder is associated with JNK overexpression, such suppressive JNK inhibitor peptides can be introduced to a cell. In some instances, "modulate" may include the increase of JNK expression, for example by use of an IB peptide-specific antibody that blocks the binding of an IB-peptide to JNK, thus preventing JNK inhibition by the IB-related peptide.

The JNK inhibitor, peptides, fusion peptides and nucleic acids of the invention can be formulated in pharmaceutical compositions. These compositions may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal or patch routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, peptide, or nucleic acid molecule, other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980.

Alternatively, targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, e.g. in a viral vector (a variant of the VDEPT technique—see below). The vector could be targeted to the specific cells to be treated, or it could contain regulatory elements, which are switched on more or less selectively by the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, e.g. a JNK inhibitor peptide, in a vector by expression from encoding DNA in a viral vector (see for example, EP-A-415731 and WO 90/07936).

In a specific embodiment of the present invention, nucleic acids include a sequence that encodes a JNK inhibitor peptide, or functional derivatives thereof, are administered to modulate activated JNK signaling pathways by way of gene therapy. In more specific embodiments, a nucleic acid or nucleic acids encoding a JNK inhibitor peptide, or functional derivatives thereof, are administered by way of gene therapy. Gene therapy refers to therapy that is performed by the administration of a specific nucleic acid to a subject. In this embodiment of the present invention, the nucleic acid produces its encoded peptide(s), which then serve to exert a therapeutic effect by modulating function of the disease or disorder. Any of the methodologies relating to gene therapy available within the art may be used in the practice of the present invention. See e.g., Goldspiel, et al., 1993. *Clin Pharm* 12: 488-505.

In a preferred embodiment, the Therapeutic comprises a nucleic acid that is part of an expression vector expressing any one or more of the IB-related peptides, or fragments, derivatives or analogs thereof, within a suitable host. In a specific embodiment, such a nucleic acid possesses a promoter that is operably-linked to coding region(s) of a JNK inhibitor peptide. The promoter may be inducible or constitutive, and, optionally, tissue-specific. In another specific embodiment, a nucleic acid molecule is used in which coding sequences (and any other desired sequences) are flanked by regions that promote homologous recombination at a desired site within the genome, thus providing for infra-chromosomal expression of nucleic acids. See e.g., Koller and Smithies, 1989. *Proc Natl Acad Sci USA* 86: 8932-8935.

Delivery of the Therapeutic nucleic acid into a patient may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. In a specific embodiment of the present invention, a nucleic acid is directly administered in vivo, where it is expressed to produce the encoded product. This may be accomplished by any of numerous methods known in the art including, e.g., constructing the nucleic acid as part of an appropriate nucleic acid expression vector and administering the same in a manner such that it becomes intracellular (e.g., by infection using a defective or attenuated retroviral or other viral vector; see U.S. Pat. No. 4,980,286); directly injecting naked DNA; using microparticle bombardment (e.g., a "GENE GUN®; Biolistic, DuPont); coating the nucleic acids with lipids; using associated cell-surface receptors/transfecting agents; encapsulating in liposomes, microparticles, or microcapsules; administering it in linkage to a peptide that is known to enter the nucleus; or by administering it in linkage to a ligand predisposed to receptor-mediated endocytosis (see, e.g., Wu and Wu, 1987. *J Biol Chem* 262: 4429-4432), which can be used to "target" cell types that specifically express the receptors of interest, etc.

An additional approach to gene therapy in the practice of the present invention involves transferring a gene into cells in in vitro tissue culture by such methods as electroporation, lipofection, calcium phosphate-mediated transfection, viral infection, or the like. Generally, the method of transfer includes the concomitant transfer of a selectable marker to the cells. The cells are then placed under selection pressure (e.g., antibiotic resistance) so as to facilitate the isolation of those cells that have taken up, and are expressing, the transferred gene. Those cells are then delivered to a patient. In a specific embodiment, prior to the in vivo administration of the resulting recombinant cell, the nucleic acid is introduced into a cell by any method known within the art including, e.g., transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies that ensure that the necessary developmental and physiological functions of the recipient cells are not disrupted by the transfer. See e.g., Loeffler and Behr, 1993. *Meth Enzymol* 217: 599-618. The chosen technique should provide for the stable transfer of the nucleic acid to the cell, such that the nucleic acid is expressible by the cell. Preferably, the transferred nucleic acid is heritable and expressible by the cell progeny.

In preferred embodiments of the present invention, the resulting recombinant cells may be delivered to a patient by various methods known within the art including, e.g., injection of epithelial cells (e.g., subcutaneously), application of recombinant skin cells as a skin graft onto the patient, and intravenous injection of recombinant blood cells (e.g., hematopoietic stem or progenitor cells). The total amount of cells that are envisioned for use depend upon the desired effect, patient state, and the like, and may be determined by one skilled within the art.

Cells into which a nucleic acid can be introduced for purposes of gene therapy encompass any desired, available cell type, and may be xenogeneic, heterogeneic, syngeneic, or autogeneic. Cell types include, but are not limited to, differentiated cells such as epithelial cells, endothelial cells, keratinocytes, fibroblasts, muscle cells, hepatocytes and blood cells, or various stem or progenitor cells, in particular embryonic heart muscle cells, liver stem cells (International Patent Publication WO 94/08598), neural stem cells (Stemple and Anderson, 1992, *Cell* 71: 973-985), hematopoietic stem or progenitor cells, e.g., as obtained from bone marrow, umbilical cord blood, peripheral blood, fetal liver, and the like. In a preferred embodiment, the cells utilized for gene therapy are autologous to the patient.

Immunoassays

The peptides and antibodies of the present invention may be utilized in assays (e.g., immunoassays) to detect, prognose, diagnose, or monitor various conditions, diseases, and disorders characterized by aberrant levels of JNK, or a JNK inhibitor peptide, or monitor the treatment thereof. An "aberrant level" means an increased or decreased level in a sample relative to that present in an analogous sample from an unaffected part of the body, or from a subject not having the disorder. The immunoassay may be performed by a method comprising contacting a sample derived from a patient with an antibody under conditions such that immunospecific-binding may occur, and subsequently detecting or measuring the amount of any immunospecific-binding by the antibody. In a specific embodiment, an antibody specific for a JNK inhibitor peptide may be used to analyze a tissue or serum sample from a patient for the presence of JNK or a JNK inhibitor peptide; wherein an aberrant level of JNK or a JNK inhibitor peptide is indicative of a diseased condition. The immunoassays that may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, fluorescent immunoassays, complement-fixation assays, immunoradiometric assays, and protein-A immunoassays, etc.

Kits

The present invention additionally provides kits for diagnostic or therapeutic use that include one or more containers containing an anti-JNK inhibitor peptide antibody and, optionally, a labeled binding partner to the antibody. The label incorporated into the antibody may include, but is not limited to, a chemiluminescent, enzymatic, fluorescent, colorimetric or radioactive moiety. In another specific embodiment, kits for diagnostic use that are comprised of one or more containers containing modified or unmodified nucleic acids that encode, or alternatively, that are the complement to, a JNK inhibitor peptide and, optionally, a labeled binding partner to the nucleic acids, are also provided. In an alternative specific embodiment, the kit may comprise, in one or more containers, a pair of oligonucleotide primers (e.g., each 6-30 nucleotides in length) that are capable of acting as amplification primers for polymerase chain reaction (PCR; see, e.g., Innis, et al., 1990. PCR PROTOCOLS, Academic Press, Inc., San Diego, Calif.), ligase chain reaction, cyclic probe reaction, and the like, or other methods known within the art. The kit may, optionally, further comprise a predetermined amount of a purified JNK inhibitor peptide, or nucleic acids thereof, for use as a diagnostic, standard, or control in the assays.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

SPECIFIC EXAMPLES

Example 1

Identification of JNK Inhibitor Peptides

Amino acid sequences important for efficient interaction with JNK were identified by sequence alignments between known JBDs. Sequence comparison between the JBDs of IB1 [SEQ ID NO:17], IB2 [SEQ ID NO:18], c-Jun [SEQ ID NO:19] and ATF2 [SEQ ID NO:20] defined a weakly conserved 8 amino acid sequence (FIG. 1A). Since the JBDs of IB1 and IB2 are approximately 100 fold as efficient as c-Jun or ATF2 in binding JNK (Dickens et al. Science 277: 693 (1997), it was reasoned that conserved residues between IB1 and IB2 must be important to confer maximal binding. The comparison between the JBDs of IB1 and IB2 defined two blocks of seven and three amino acids that are highly conserved between the two sequences. These two blocks are contained within a peptide sequence of 23 amino acids in IB1 [SEQ ID NO:1] and 21 amino acid IB2 [SEQ ID NO:2]. These sequences are shown in FIG. 1B, dashes in the IB2 sequence indicate a gap in the sequence in order to align the conserved residues.

Example 2

Preparation of JNK Inhibitor Fusion Proteins

JNK inhibitor fusion proteins were synthesized by covalently linking the C-terminal end of $JBD_{23}$ or the 21 amino acid sequence derived from the JBD of IB2 ($JBD_{21}$) to a N-terminal 10 amino acid long carrier peptide derived from the HIV-$TAT_{48-57}$ Vives et al., J. Biol. Chem. 272: 16010 (1997)) via a spacer consisting of two proline residues. This spacer was used to allow for maximal flexibility and prevent unwanted secondary structural changes. As shown in FIG. 1C, these preparations were designated L-TAT [SEQ ID NO:7], L-TAT-IB1 [SEQ ID NO:11] and L-TAT-IB2 [SEQ ID NO:12], respectively. All-D retro-inverso peptides TAT-fusion peptides were also synthesized and were designated D-TAT [SEQ ID NO:8] and D-TAT-IB1 [SEQ ID NO:14], respectively. All D and L peptides were produced by classical F-mock synthesis and further analysed by Mass Spectrometry. They were finally purified by HPLC. To determine the effects of the proline spacer, two types of TAT peptide were produced one with and one without two prolines. The addition of the two prolines did not appear to modify the entry or the localization of the TAT peptide inside cells.

Generic peptides showing the conserved amino acid residues are given in FIG. 2. An "X" indicates any amino acid. The number of Xs in a given peptide is not limited to the one depicted, and may vary. See above for a more detailed description of the generic sequences.

Example 3

Inhibition of βCell Death by $JBD_{23}$

Effects of the 23 a.a. long JBD sequence of IB1 on JNK biological activities were then studied. The 23 a.a. sequence was linked N-terminal to the Green Fluorescent Protein (GFP-$JBD_{23}$ construct), and the effect of this construct on pancreatic β-cell apoptosis induced by IL-1β was evaluated. See FIG. 3. This mode of apoptosis was previously shown to be blocked by transfection with $JBD_{1-280}$, whereas specific inhibitors of ERK1/2 or p38 did not protect. See Ammendrup et al, supra.

Oligonucleotides corresponding to the 23 amino acid sequence ($JBD_{23}$; FIG. 1B) and a sequence mutated at the fully conserved regions ($JBD_{23mut}$) were synthesized and directionally inserted into the EcoRI and SalI sites of the pEGFP-N1 vector encoding the Green Fluorescent Protein (GFP) (from Clontech). Insulin producing βTC-3 cells were cultured in RPMI 1640 medium supplemented with 10% Fetal Calf Serum, 100 µg/mL Streptomycin, 100 units/mL Penicillin and 2 mM Glutamine. Insulin producing βTC-3 cells were transfected with the indicated vectors and IL-1β (10 ng/mL) was added to the cell culture medium. The number of apoptotic cells were counted at 48 hours after the addition of IL-1β using an inverted fluorescence microscope. Apoptotic cells were discriminated from normal cells by the characteristic "blebbing out" of the cytoplasm were counted after two days.

As indicated in FIG. 3, GFP is Green Fluorescent protein expression vector used as a control; JBD23 is the vector expressing a chimeric GFP linked to the 23 a.a. sequence from the JBD of IB1; JBD23Mut is the same vector as GFP- JBD23, but with a JBD mutated at four conserved residues shown as FIG. 1B; and JBD280 is the GFP vector linked to the entire JBD (a.a. 1-280). The GFP-JBD$_{23}$ expressing construct prevented IL-1β induced pancreatic β-cell apoptosis as efficiently as the entire JBD$_{1-280}$ (FIG. 3, JBD23/IL-1 compared to JBD280/IL-1). As additional controls, sequences mutated at fully conserved IB1 residues had greatly decreased ability to prevent apoptosis (FIG. 3, JBD23Mut/IL-1).

Example 4

Cellular Import of TAT-IB1 and TAT-IB2 Peptides

The ability of the L- and D-enantiomeric forms of TAT, TAT-IB1 and TAT-IB2 peptides ("TAT-IB peptides") to enter cells were evaluated.

L-TAT, D-TAT, L-TAT-IB1, L-TAT-IB2 and D-TAT-IB1 peptides [SEQ ID NOs:7, 8, 11, 12 and 14, respectively] were labeled by N-terminal addition of a glycine residue conjugated to fluorescein. Labeled peptides (1 µM) were added to βTC-3 cell cultures, which were maintained as described in Example 3. At predetermined times, cells were washed with PBS and fixed for five minutes in ice-cold methanol-acetone (1:1) before being examined under a fluorescence microscope. Fluorescein-labeled BSA (1 µM, 12 moles/mole BSA) was used as a control. Results demonstrated that all the above fluorescein labeled peptides had efficiently and rapidly (less than five minutes) entered cells once added to the culture medium. Conversely, fluorescein labeled bovine serum albumin (1 µM BSA, 12 moles fluorescein/mole BSA) did not enter the cells.

A time course study indicated that the intensity of the fluorescent signal for the L-enantiomeric peptides decreased by 70% following a 24 hours period. Little to no signal was present at 48 hours. In contrast, D-TAT and D-TAT-IB1 were extremely stable inside the cells. Fluorescent signals from these all-D retro-inverso peptides were still very strong 1 week later, and the signal was only slightly diminish at 2 weeks post treatment.

Example 5

In Vitro Inhibition of c-JUN, ATF2 and Elk1 Phosphorylation

Figure 4A:
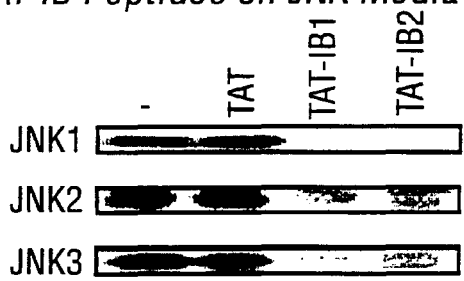
FIG. 4 is an illustration demonstrating the effects of TAT, TAT-IB1 and TAT-IB2 peptides on phosphorylation of recombinant JNKs. Panel A shows inhibition of c-Jun, ATF2 and Elk1 phosphorylation by recombinant JNKs in vitro. Panel B shows dose response experiments similar to Panel A.

The effects of the peptides on JNKs-mediate phosphorylation of their target transcription factors were investigated in vitro. Recombinant and nonactivated JNK1, JNK2 and JNK3 were produced using a TRANSCRIPTION AND TRANSLATION rabbit reticulocyte lysate kit (Promega) and used in solid phase kinase assays with c-Jun, ATF2 and Elk1, either alone or fused to glutathione-S-transferase (GST), as substrates. Dose response studies were performed wherein L-TAT, L-TAT-IB1 or L-TAT-IB2 peptides (0-25 µM) were mixed with the recombinant JNK1, JNK2, or JNK3 kinases in reaction buffer (20 mM Tris-acetate, 1 mM EGTA, 10 mM p-nitrophenyl-phosphate (pNPP), 5 mM sodium pyrophosphate, 10 mM p-glycerophosphate, 1 mM dithiothreitol) for 20 minutes. The kinase reactions were then initiated by the addition of 10 mM MgCl$_2$ and 5 µCi$^{33}$P-γ-dATP and 1 µg of either GST-Jun (a.a. 1-89), GST-AFT2 (a.a. 1-96) or GST-ELK1 (a.a. 307-428). GST-fusion proteins were purchased from Stratagene (La Jolla, Calif.). Ten µL of glutathione-agarose beads were also added to the mixture. Reaction products were then separated by SDS-PAGE on a denaturing 10% polyacrylamide gel. Gels were dried and subsequently exposed to X-ray films (Kodak). Nearly complete inhibition of c-Jun, ATF2 and Elk1 phosphorylation by JNKs was observed at TAT-IB peptide doses as low as 2.5 µM. However, a marked exception was the absence of TAT-IB inhibition of JNK3 phosphorylation of Elk1. Overall, the TAT-IB1 peptide appeared slightly superior to TAT-IB2 in inhibiting JNK family phosphorylation of their target transcription factors. (See, FIG. 4A).

Figure 4B:
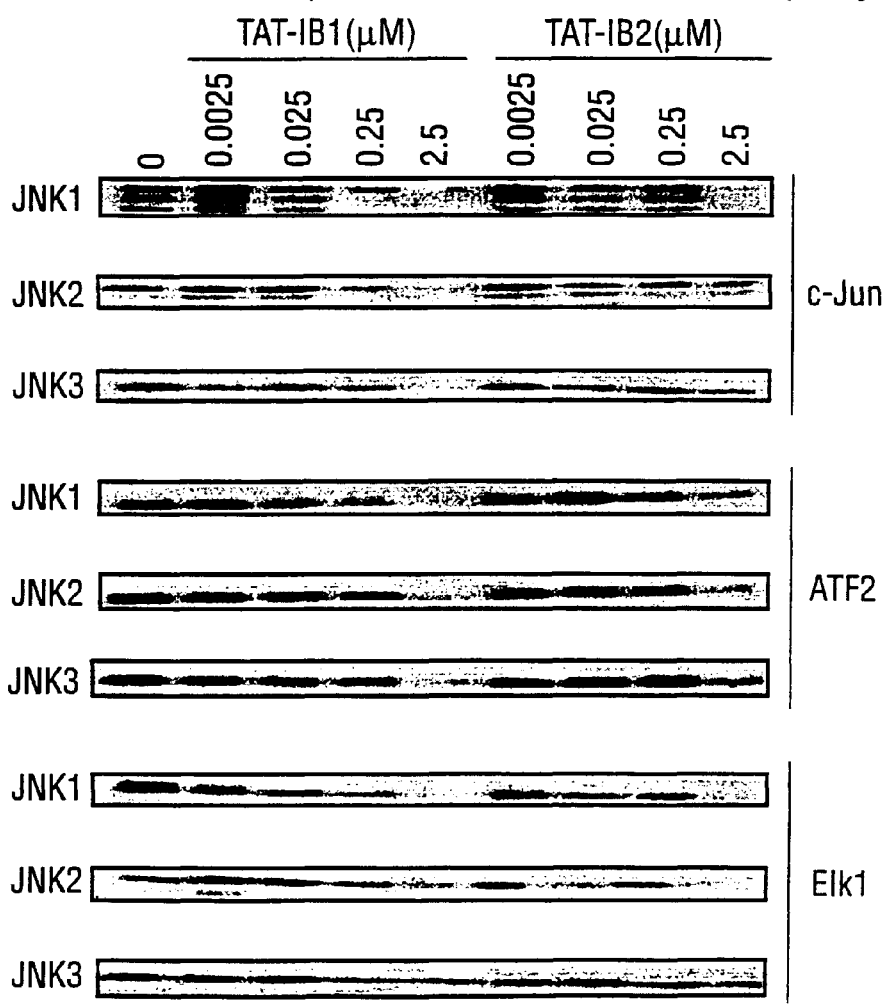

The ability of D-TAT, D-TAT-IB1 and L-TAT-IB1 peptides (0-250 µM dosage study) to inhibit GST-Jun (a.a. 1-73) phosphorylation by recombinant JNK1, JNK2, and JNK3 by were analyzed as described above. Overall, D-TAT-IB1 peptide decreased JNK-mediated phosphorylation of c-Jun, but at levels approximately 10-20 fold less efficiently than L-TAT-IB1. (See, FIG. 4B).

Example 6

Inhibition of c-JUN Phosphorylation by Activated JNKs

Figure 6:
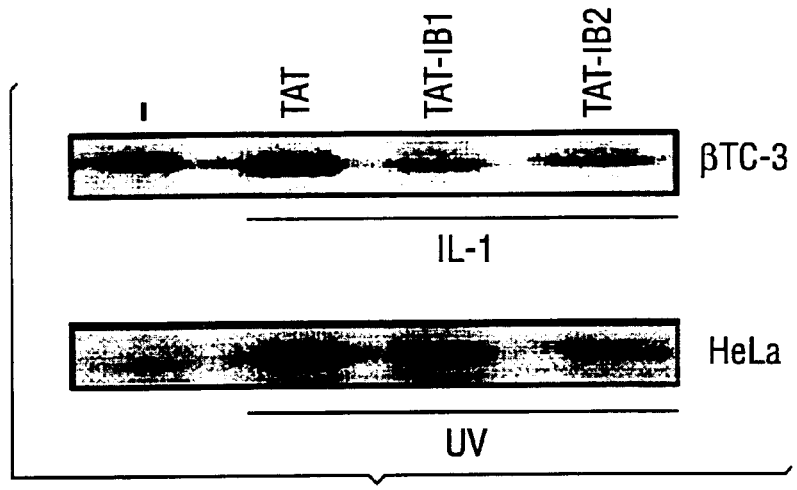
FIG. 6 is an illustration demonstrating the inhibition of c-Jun phosphorylation by activated JNKs.

The effects of the L-TAT, L-TAT-IB1 or L-TAT-IB2 peptides on JNKs activated by stressful stimuli were evaluated using GST-Jun to pull down JNKs from UV-light irradiated HeLa cells or IL-1β treated βTC cells. βTC cells were cultured as described above. HeLa cells were cultured in DMEM medium supplemented with 10% Fetal Calf Serum, 100 µg/mL Streptomycin, 100 units/ml Penicillin and 2 mM Glutamine. One hour prior to being used for cell extract preparation, βTC cells were activated with IL-1β as described above, whereas HeLa cells were activated by UV-light (20 J/m$^2$). Cell extracts were prepared from control, UV-light irradiated HeLa cells and IL-1β treated βTC-3 cells by scraping the cell cultures in lysis buffer (20 mM Tris-acetate, 1 mM EGTA, 1% Triton X-100, 10 mM p-nitrophenyl-phosphate, 5 mM sodium pyrophosphate, 10 mM β-glycerophosphate, 1 mM dithiothretiol). Debris was removed by centrifugation for five minutes at 15,000 rpm in an SS-34 Beckman rotor. One-hundred µg extracts were incubated for one hour at room temperature with one µg GST-jun (amino acids 1-89) and 10 µL of glutathione-agarose beads (Sigma). Following four washes with the scraping buffer, the beads were resuspended in the same buffer supplemented with L-TAT, L-TAT-IB1 or L-TAT-IB2 peptides (25 µM) for 20 minutes. Kinase reactions were then initiated by the addition of 10 mM MgCl$_2$ and 5 µ Ci $^{33}$P-γ-dATP and incubated for 30 minutes at 30° C. Reaction products were then separated by SDS-PAGE on a denaturing 10% polyacrylamide gel. Gels were dried and subsequently exposed to X-ray films (Kodak). The TAT-IB peptides efficiently prevented phosphorylation of c-Jun by activated JNKs in these experiments. (See, FIG. 6).

Example 7

In Vivo Inhibition of c-JUN Phosphorylation by TAT-IB Peptides

To determine whether the cell-permeable peptides could block JNK signaling in vivo, we used a heterologous GAL4 system. HeLa cells, cultured as described above, were co-transfected with the 5×GAL-LUC reporter vector together with the GAL-Jun expression construct (Stratagene) comprising the activation domain of c-Jun (amino acids 1-89) linked to the GAL4 DNA-binding domain. Activation of JNK was achieved by the co-transfection of vectors expressing the directly upstream kinases MKK4 and MKK7 (See, Whitmarsh et al., Science 285: 1573 (1999)). Briefly, 3×10$^5$ cells were trasfected with the plasmids in 3.5-cm dishes using DOTAP (Boehringer Mannheim) following instructions from the manufacture. For experiments involving GAL-Jun, 20 ng of the plasmid was transfected with 1 µg of the reporter plasmid pFR-Luc (Stratagene) and 0.5 µg of either MKK4 or MKK7 expressing plasmids. Three hours following transfection, cell media were changed and TAT, TAT-IB1, and TAT-IB2 peptides (1 µM) were added. The luciferase activities were measured 16 hours later using the "Dual Reporter System" from Promega after normalization to protein content. As shown in FIG. 5, addition of both the TAT-IB1 and TAT-IB2 peptides blocked activation of c-Jun following MKK4 and MKK7 mediated activation of JNK. Because HeLa cells express both JNK1 and JNK2 isoforms but not JNK3, we transfected cells with JNK3. Again, the two TAT-IB peptides inhibited JNK2 mediated activation of c-Jun.

Example 8

Inhibition of IL-1β Induced Pancreatic β-Cell Death by TAT-IB Peptides

We investigated the effects of the L-TAT-IB peptides on the promotion of pancreatic β-cell apoptosis elicited by IL-1β. βTC-3 cell cultures were incubated for 30 minutes with 1 µM of either L-TAT-IB1 or L-TAT-IB2 peptides followed by 10 ng/mL of IL-1β. A second addition of peptide (1 µM) was performed 24 hours later. Apoptotic cells were counted after two days of incubation with IL-1β using Propidium Iodide (red stained cell are dead cells) and Hoechst 33342 (blue stained cell are cells with intact plasma membrane) nuclear staining. As shown in FIG. 5, addition of the TAT-IB peptides inhibited IL-1β-induced apoptosis of βTC-3 cells cultured in the presence of IL-1β for two days.

Long term inhibition of IL-1β induced cells death was examined by treating βTC-3 cells as described above, except that incubation of the cells with the peptides and IL-1β was sustained for 12 days. Additional peptides (1 µM) were added each day and additional IL-1β (10 ng/mL) was added every 2 days. The TAT-IB1 peptide confers strong protection against apoptosis in these conditions. Taken together, these experiments establish that TAT-IB peptides are biologically active molecules able to prevent the effects of JNK signaling on cell fate.

Example 9

Synthesis of an All-D-Retro-Inverso Peptides

Peptides of the invention may be all-D amino acid peptides synthesized in reverse to prevent natural proteolysis (i.e., all-D-retro-inverso peptides). An all-D retro-inverso peptide of the invention would provide a peptide with functional properties similar to the native peptide, wherein the side groups of the component amino acids would correspond to the native peptide alignment, but would retain a protease resistant backbone.

Retro-inverso peptides of the invention are analogs synthesized using D-amino acids by attaching the amino acids in a peptide chain such that the sequence of amino acids in the retro-inverso peptide analog is exactly opposite of that in the selected peptide which serves as the model. To illustrate, if the naturally occurring TAT protein (formed of L-amino acids) has the sequence GRKKRRQRRR [SEQ ID NO:7], the retro-inverso peptide analog of this peptide (formed of D-amino acids) would have the sequence RRRQRRKKRG [SEQ ID NO:8]. The procedures for synthesizing a chain of D-amino acids to form the retro-inverso peptides are known in the art.

See, e.g., Jameson et al., Nature, 368, 744-746 (1994); Brady et al., Nature, 368, 692-693 (1994)); Guichard et al., J. Med. Chem. 39, 2030-2039 (1996). Specifically, the retro-peptides were produced by classical F-mock synthesis and further analysed by Mass Spectrometry. They were finally purified by HPLC.

Since an inherent problem with native peptides is degradation by natural proteases and inherent immunogenicity, the heterobivalent or heteromultivalent compounds of this invention will be prepared to include the "retro-inverso isomer" of the desired peptide. Protecting the peptide from natural proteolysis should therefore increase the effectiveness of the specific heterobivalent or heteromultivalent compound, both by prolonging half-life and decreasing the extent of the immune response aimed at actively destroying the peptides.

Example 10

Long Term Biological Activity of All-D-Retro-Inverso IB Peptides

Long term biological activity is predicted for the D-TAT-IB retro-inverso containing peptide heteroconjugate when compared to the native L-amino acid analog owing to protection of the D-TAT-IB peptide from degradation by native proteases, as shown in Example 5.

Figure 10:
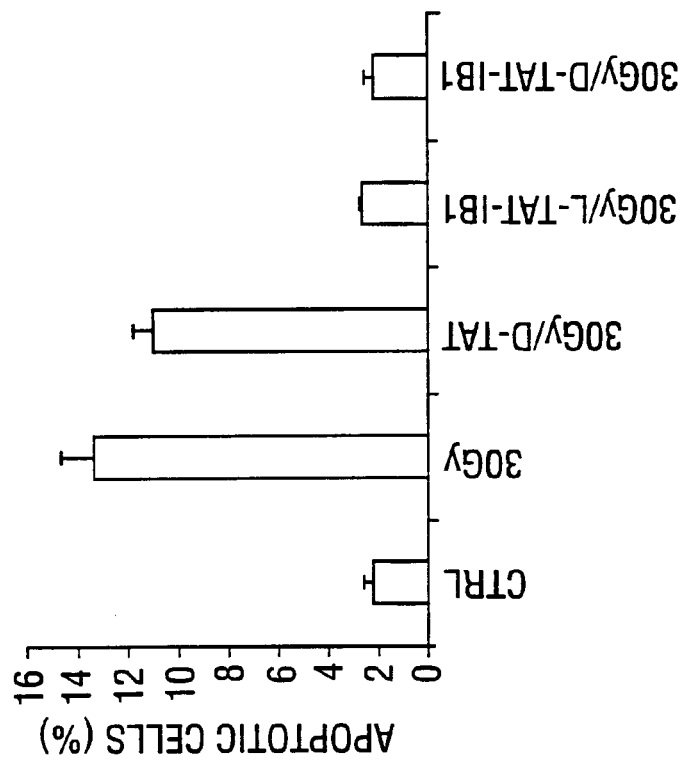
FIG. 10 is a histogram depicting inhibition of irradiation induced human colon cancer WiDr cell death by L-TAT-IB1 and D-TAT-IB1 peptides.

Inhibition of IL-1β induced pancreatic β-cell death by the D-TAT-IB1 peptide was analyzed. As shown in FIG. 10, βTC-3 cells were incubated as described above for 30 minutes with one single addition of the indicated peptides (1 µM), then IL-1β (10 ng/ml) was added. Apoptotic cells were then counted after two days of incubation with IL-1β by use of Propidium Iodide and Hoechst 33342 nuclear staining A minimum of 1,000 cells were counted for each experiment. Standard Error of the Means (SEM) are indicated, n=5. The D-TAT-IB1 peptide decreased IL-1 induced apoptosis to a similar extent as L-TAT-IB peptides (compare FIG. 5 and FIG. 10).

Figure 9:
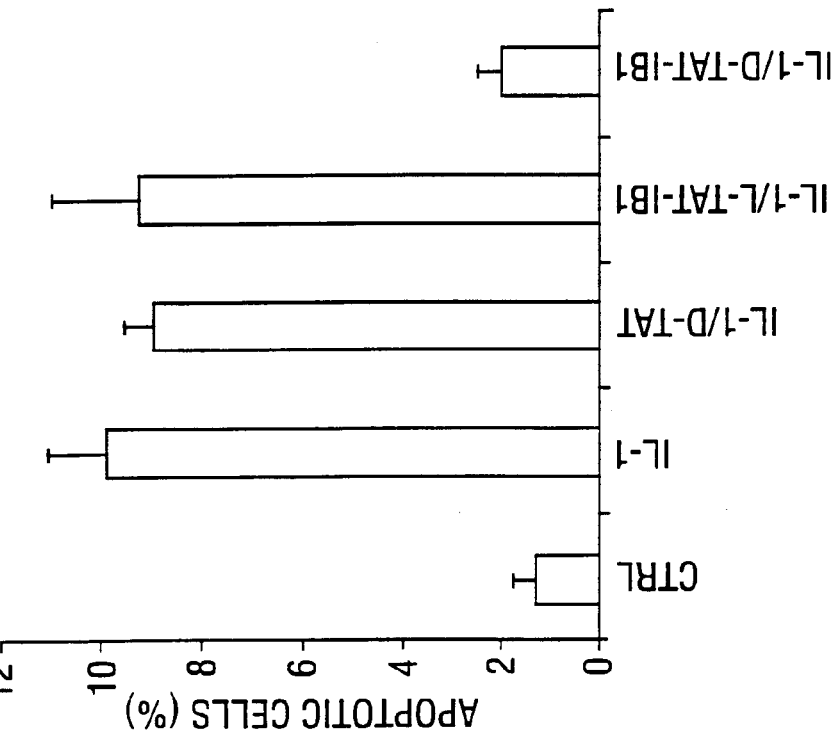
FIG. 9 is a histogram depicting long term inhibition of IL-1β induced pancreatic β-cell death by L-TAT-IB1 and D-TAT-IB1 peptides.

Long term inhibition of IL-1β induced cell-death by the D-TAT-IB1 peptide was also analyzed. βTC-3 cells were incubated as above for 30 minutes with one single addition of the indicated peptides (1 µM), then IL-1β (10 ng/ml) was added, followed by addition of the cytokine every two days. Apoptotic cells were then counted after 15 days of incubation with IL-1β by use of Propidium Iodide and Hoechst 33342 nuclear staining Note that one single addition of the L-TAT-IB1 peptide does not confer long-term protection. A minimum of 1,000 cells were counted for each experiment. Standard Error of the Means (SEM) are indicated, n=5. Results are shown in FIG. 9. D-TAT-IB1, but not L-TAT-IB1, was able to confer long term (15 day) protection.

Example 11

Inhibition of Irradiation Induced Pancreatic β-Cell Death by TAT-IB Peptides

JNK is also activated by ionizing radiation. To determine whether TAT-IB peptides would provide protection against radiation-induced JNK damage, "WiDr" cells were irradiated (30Gy) in presence or absence of D-TAT, L-TAT-IB1 or D-TAT-IB1 peptides (1 µM added 30 minutes before irradiation), as indicated in FIG. 10. Control cells (CTRL) were not irradiated. Cells were analyzed 48 hours later by mean of PI and Hoechst 33342 staining, as described above. n=3, SEM are indicated. L-TAT-IB1 and D-TAT-IB1 peptides were both able to prevent irradiation induced apoptosis in this human colon cancer cell line.

Example 12

Radioprotection to Ionizing Radiation by TAT-IB Peptides

To determine the radioprotective effects of the TAT-IB peptides, C57 Bl/6 mice (2 to 3 months old) were irradiated with a Phillips RT 250 R-ray at a dose rate of 0.74 Gy/min (17 mA, 0.5 mm Cu filter). Thirty minutes prior to irradiation, the animals were injected i.p. with either the TAT, L-TAT-IB1 and D-TAT-IB1 peptides (30 µl of a 1 mM solution). Briefly, mice were irradiated as follows: mice were placed in small plastic boxes with the head lying outside the box. The animals were placed on their back under the irradiator, and their neck fixed in a small plastic tunnel to maintain their head in a correct position. The body was protected with lead. Prior to irradiation mice were maintained on standard pellet mouse chow, however post irradiation mice were fed with a semi-liquid food that was renewed each day.

The reaction of the lip mucosa was then scored by 2 independent observers according to the scoring system developed by Parkins et al. (Parkins et al, Radiotherapy & Oncology, 1: 165-173, 1983), in which the erythema status as well as the presence of edema, desquamation and exudation was quoted. Additionally, animals were weighed before each recording of their erythema/edema status.

FIG. 12A: illustrated the weight of the mice following irradiation. Values are reported to the initial weight of the mice that was set to 100. CTRL: control mice injected with 30 µl of a saline solution. n=2 for each values reported, S.D. are indicated. x values are days FIG. 12B is illustrative of the erythema/edema scoring following irradiation. The edema and erythema status of the ventral lip of the same mice as in FIG. 12A was quantified. n=2 for each value reported. x values are days The results of these experiments indicate that the TAT-IB Peptides can protect against weight loss and erythema/edema associated with ionizing radiation.

Example 13

Suppression of JNK Transcription Factors by L-TAT-IB1 Peptides

Figure 11:
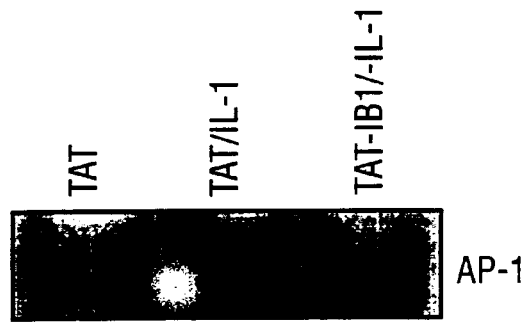
FIG. 11 is an illustration of the modulation of JNK kinase activity by L-TAT, TAT-IB1 and D-TAT-IB1 peptides.
Figure 8:
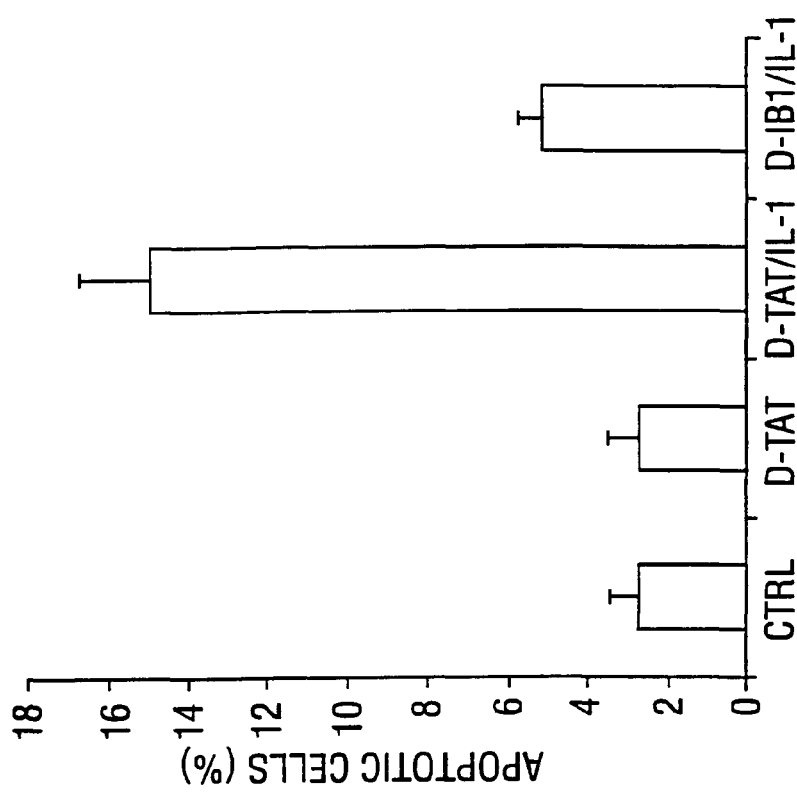
FIG. 8 is a histogram depicting short term inhibition of IL-1β induced pancreatic β-cell death by the D-TAT-IB peptides.
Figure 7:
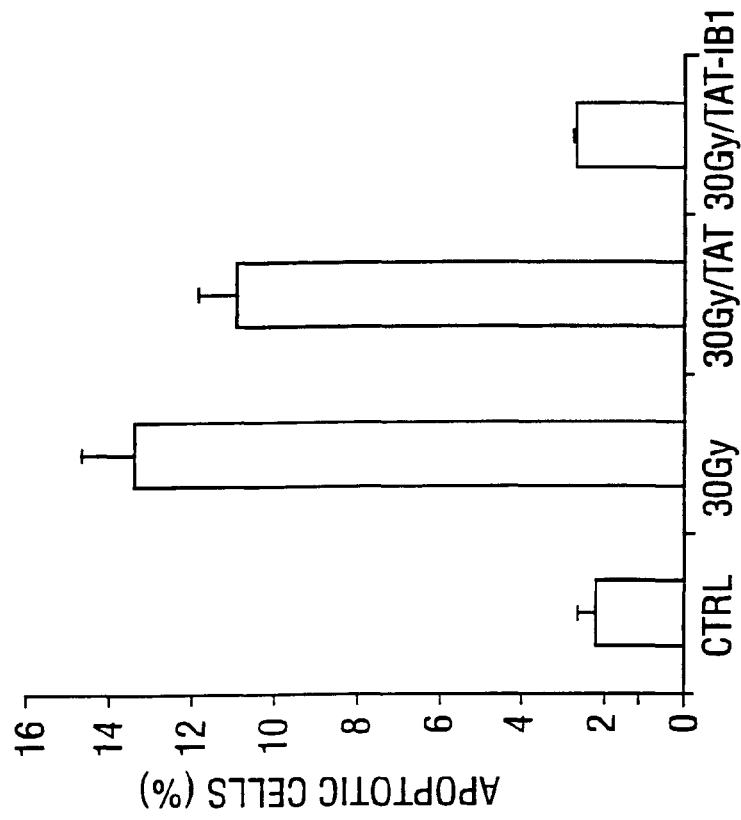
FIG. 7 is a histogram depicting short term inhibition of IL-1β induced pancreatic β-cell death by the L-TAT-IB peptides.

Gel retardation assays were carried out with an AP-1 doubled labeled probe (5'-CGC TTG ATG AGT CAG CCG GAA-3' (SEQ ID NO: 21). HeLa cell nuclear extracts that were treated or not for one hour with 5 ng/ml TNF-α, as indicated. TAT and L-TAT-IB1 peptides were added 30 minutes before TNF-α. Only the part of the gel with the specific AP-1 DNA complex (as demonstrated by competition experiments with non-labeled specific and non-specific competitors) is shown. L-TAT-IB1 peptides decrease the formation of the AP-1 DNA binding complex in the presence of TNF-α. (See, FIG. 11).

EQUIVALENTS

From the foregoing detailed description of the specific embodiments of the invention, it should be apparent that unique cell-permeable bioactive peptides have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

What is claimed is:

1. A chimeric peptide capable of inhibiting the activation of at least one c-jun amino terminal kinase (JNK) signaling pathway, said chimeric peptide being 35 amino acids or less in length, comprising a first domain and a second domain linked by a covalent bond at either the N-terminal or the C-terminal end of the first domain, wherein the first domain comprises the amino acid sequence of SEQ ID NO: 8, and the second domain comprises a JNK inhibitor sequence selected from the group consisting of
   a) a peptide with the amino acid sequence of SEQ ID NO:3 and
   b) a peptide having at least 80% sequence identity to SEQ ID NO:3,
   wherein the JNK inhibitor sequence is capable of inhibiting the activation of at least one JNK signaling pathway.

2. The chimeric peptide of claim 1, wherein the first domain augments cellular uptake of the peptide.

3. The chimeric peptide of claim 1, wherein the first domain directs nuclear localization of the peptide.

4. The chimeric peptide of claim 1, wherein the JNK inhibitor sequence binds c-Jun amino terminal kinase (JNK).

5. The chimeric peptide of claim 1, wherein the JNK signaling pathway comprises at least one transcription factor selected from the group consisting of c-Jun, ATF2, and Elk 1.

6. A peptide consisting of the amino acid sequence of SEQ ID NO:3.

7. A pharmaceutical composition comprising the chimeric peptide of any of claims 1-5 and a pharmaceutically acceptable carrier.

* * * * *

SEQUENCE LISTING

<160> NUMBER OF SEQ ID NOS: 21

<210> SEQ ID NO 1
<211> LENGTH: 23
<212> TYPE: PRT
<213> ORGANISM: Artificial Sequence
<220> FEATURE:
<223> OTHER INFORMATION: chemically synthesized

<400> SEQUENCE: 1

Asp Thr Tyr Arg Pro Lys Arg Pro Thr Thr Leu Asn Leu Phe Pro Gln
1               5                   10                  15

Val Pro Arg Ser Gln Asp Thr
            20

<210> SEQ ID NO 2
<211> LENGTH: 21
<212> TYPE: PRT
<213> ORGANISM: Artificial Sequence
<220> FEATURE:
<223> OTHER INFORMATION: chemically synthesized

<400> SEQUENCE: 2

Glu Glu Pro His Lys His Arg Pro Thr Thr Leu Arg Leu Thr Thr Leu
1               5                   10                  15

Gly Ala Gln Asp Ser
            20

<210> SEQ ID NO 3

<400> SEQUENCE: 3

000

<210> SEQ ID NO 4

<400> SEQUENCE: 4

000

<210> SEQ ID NO 5
<211> LENGTH: 19
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: may be any amino acid and may or may not be
      present as defined in the specification
<220> FEATURE:
<221> NAME/KEY: MISC_FEATURE
<222> LOCATION: (7)..(7)
<223> OTHER INFORMATION: may be any amino acid
<220> FEATURE:
<221> NAME/KEY: MISC_FEATURE
<222> LOCATION: (9)..(15)
<223> OTHER INFORMATION: may be any amino acid
<220> FEATURE:
<221> NAME/KEY: MISC_FEATURE
<222> LOCATION: (18)..(18)
<223> OTHER INFORMATION: may be Ser or Thr
<220> FEATURE:
<221> NAME/KEY: MISC_FEATURE
<222> LOCATION: (19)..(19)
<223> OTHER INFORMATION: may be any amino acid and may or may not be
      present as defined in the specification

<400> SEQUENCE: 5

Xaa Arg Pro Thr Thr Leu Xaa Leu Xaa Xaa Xaa Xaa Xaa Xaa Xaa Gln
1               5                   10                  15

Asp Xaa Xaa

<210> SEQ ID NO 6

<400> SEQUENCE: 6

000

<210> SEQ ID NO 7
<211> LENGTH: 10
<212> TYPE: PRT
<213> ORGANISM: Artificial Sequence
<220> FEATURE:
<223> OTHER INFORMATION: chemically synthesized

<400> SEQUENCE: 7

Gly Arg Lys Lys Arg Arg Gln Arg Arg Arg
1               5                   10

<210> SEQ ID NO 8

<400> SEQUENCE: 8

000

```
<210> SEQ ID NO 9
<211> LENGTH: 17
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: may be any amino acid and may or may not be
      present as defined in the specification
<220> FEATURE:
<221> NAME/KEY: misc_feature
<222> LOCATION: (2)..(4)
<223> OTHER INFORMATION: may be any amino acid
<220> FEATURE:
<221> NAME/KEY: misc_feature
<222> LOCATION: (14)..(16)
<223> OTHER INFORMATION: may be any aminio acid
<220> FEATURE:
<221> NAME/KEY: MISC_FEATURE
<222> LOCATION: (17)..(17)
<223> OTHER INFORMATION: may be any amino acid and may or may not be
      present as defined in the specification

<400> SEQUENCE: 9

Xaa Xaa Xaa Xaa Arg Lys Lys Arg Arg Gln Arg Arg Arg Xaa Xaa Xaa
1               5                   10                  15

Xaa

<210> SEQ ID NO 10

<400> SEQUENCE: 10

000

<210> SEQ ID NO 11
<211> LENGTH: 35
<212> TYPE: PRT
<213> ORGANISM: Artificial Sequence
<220> FEATURE:
<223> OTHER INFORMATION: chemically synthesized

<400> SEQUENCE: 11

Gly Arg Lys Lys Arg Arg Gln Arg Arg Arg Pro Pro Asp Thr Tyr Arg
1               5                   10                  15

Pro Lys Arg Pro Thr Thr Leu Asn Leu Phe Pro Gln Val Pro Arg Ser
                20                  25                  30

Gln Asp Thr
        35

<210> SEQ ID NO 12
<211> LENGTH: 33
<212> TYPE: PRT
<213> ORGANISM: Artificial Sequence
<220> FEATURE:
<223> OTHER INFORMATION: chemically synthesized

<400> SEQUENCE: 12

Gly Arg Lys Lys Arg Arg Gln Arg Arg Arg Pro Pro Glu Glu Pro His
1               5                   10                  15

Lys His Arg Pro Thr Thr Leu Arg Leu Thr Thr Leu Gly Ala Gln Asp
                20                  25                  30

Ser

<210> SEQ ID NO 13
```

```
<211> LENGTH: 42
<212> TYPE: PRT
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(7)
<223> OTHER INFORMATION: may be any amino acid
<220> FEATURE:
<221> NAME/KEY: misc_feature
<222> LOCATION: (17)..(24)
<223> OTHER INFORMATION: may be any amino acid
<220> FEATURE:
<221> NAME/KEY: misc_feature
<222> LOCATION: (30)..(30)
<223> OTHER INFORMATION: may be any amino acid
<220> FEATURE:
<221> NAME/KEY: misc_feature
<222> LOCATION: (32)..(38)
<223> OTHER INFORMATION: may be any amino acid
<220> FEATURE:
<221> NAME/KEY: MISC_FEATURE
<222> LOCATION: (41)..(41)
<223> OTHER INFORMATION: may be Ser or Thr
<220> FEATURE:
<221> NAME/KEY: misc_feature
<222> LOCATION: (42)..(42)
<223> OTHER INFORMATION: may be any amino acid

<400> SEQUENCE: 13

Xaa Xaa Xaa Xaa Xaa Xaa Xaa Arg Lys Lys Arg Arg Gln Arg Arg
1               5                   10                  15

Xaa Xaa Xaa Xaa Xaa Xaa Xaa Xaa Arg Pro Thr Thr Leu Xaa Leu Xaa
            20                  25                  30

Xaa Xaa Xaa Xaa Xaa Xaa Gln Asp Xaa Xaa
        35                  40

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17
<211> LENGTH: 29
<212> TYPE: PRT
<213> ORGANISM: Artificial Sequence
<220> FEATURE:
<223> OTHER INFORMATION: chemically synthesized

<400> SEQUENCE: 17

Pro Gly Thr Gly Cys Gly Asp Thr Tyr Arg Pro Lys Arg Pro Thr Thr
1               5                   10                  15

Leu Asn Leu Phe Pro Gln Val Pro Arg Ser Gln Asp Thr
            20                  25

<210> SEQ ID NO 18
```

```
<211> LENGTH: 27
<212> TYPE: PRT
<213> ORGANISM: Artificial Sequence
<220> FEATURE:
<223> OTHER INFORMATION: chemically synthesized

<400> SEQUENCE: 18

Ile Pro Ser Pro Ser Val Glu Glu Pro His Lys His Arg Pro Thr Thr
1               5                   10                  15

Leu Arg Leu Thr Thr Leu Gly Ala Gln Asp Ser
            20                  25

<210> SEQ ID NO 19
<211> LENGTH: 29
<212> TYPE: PRT
<213> ORGANISM: Artificial Sequence
<220> FEATURE:
<223> OTHER INFORMATION: chemically synthesized

<400> SEQUENCE: 19

Gly Ala Tyr Gly Tyr Ser Asn Pro Lys Ile Leu Lys Gln Ser Met Thr
1               5                   10                  15

Leu Asn Leu Ala Asp Pro Val Gly Asn Leu Lys Pro His
            20                  25

<210> SEQ ID NO 20
<211> LENGTH: 29
<212> TYPE: PRT
<213> ORGANISM: Artificial Sequence
<220> FEATURE:
<223> OTHER INFORMATION: chemically synthesized

<400> SEQUENCE: 20

Thr Asn Glu Asp His Leu Ala Val His Lys His Lys His Glu Met Thr
1               5                   10                  15

Leu Lys Phe Gly Pro Ala Arg Asn Asp Ser Val Ile Val
            20                  25

<210> SEQ ID NO 21
<211> LENGTH: 21
<212> TYPE: DNA
<213> ORGANISM: Artificial Sequence
<220> FEATURE:
<223> OTHER INFORMATION: chemically synthesized

<400> SEQUENCE: 21
cgcttgatga gtcagccgga a                                        21
```